US006670160B2

(12) United States Patent
Taylor et al.

(10) Patent No.: US 6,670,160 B2
(45) Date of Patent: Dec. 30, 2003

(54) α1,2-FUCOSYLTRANSFERASE

(75) Inventors: Diane Taylor, Edmonton (CA); Ge Wang, Edmonton (CA); Monica Palcic, Edmonton (CA)

(73) Assignee: Governors of the University of Alberta, Edmonton (CA)

( * ) Notice: Subject to any disclaimer, the term of this patent is extended or adjusted under 35 U.S.C. 154(b) by 0 days.

(21) Appl. No.: 09/848,838

(22) Filed: May 3, 2001

(65) Prior Publication Data

US 2002/0037570 A1 Mar. 28, 2002

Related U.S. Application Data

(62) Division of application No. 09/433,598, filed on Nov. 2, 1999, now Pat. No. 6,238,894.
(60) Provisional application No. 60/107,268, filed on Nov. 4, 1998.

(51) Int. Cl.$^7$ ................................................ C12N 9/10
(52) U.S. Cl. .................... 435/193; 435/183; 435/252.3; 435/252.33; 435/320.1
(58) Field of Search ................................ 435/183, 193, 435/252.3, 252.33, 320.1

(56) References Cited

U.S. PATENT DOCUMENTS

| 5,583,042 A | 12/1996 | Roth | 435/288.1 |
| 5,595,900 A | 1/1997 | Lowe | 435/193 |
| 5,643,758 A | * 7/1997 | Guan et al. | 435/69.7 |

FOREIGN PATENT DOCUMENTS

| WO | WO 98/43478 | 10/1998 |

OTHER PUBLICATIONS

Becker et al. GenBank Accession AAT05334. Jan. 31, 1996 (Alignment No. 1).*
Domino et al. Biochem J. Oct. 1, 1997, vol. 327(Pt 1), pp. 105–115.*
Saunders, N.J., et al., "Simple sequence repeats in the Helicobacter pylori genome," *Molecular Biology*, vol. 27, No. 6, Mar. 1988 , pp. 1091–1098.
Tomb, J.F. et al., "Helicobacter pylori 26695 section 9 of 134 of the complete genome," *EMBL Online Database*, XP002133092 (Aug. 25, 1997).
Beyer, T.A. et al., "Purification to homogeneity of the H blood group B–galactosidase al→2 fucosyltransferase from porcine submaxillary gland", *Journal of Biological Chemistry*, vol. 255, No. 11, 1980, pp. 5364–5372.
Wang, G. et al., "Molecular genetic basis for the variable expression of Lewis Y antigen in Helicobacter pylori: analysis of the a(1,2) fucosyltransferase gene", *Molecular Microbiology*, vol. 31, No. 4, Feb. 1999, pp. 1265–1274.

Wang, G. et al., "Novel Helicobacter pylori a1,2–fucosyltransferase, a key enzyme in the synthesis of Lewis antigen," *Microbiology*, vol. 145, No. 11, Nov. 1999, pp. 3245–3253.
Newburg, "Do the binding properties of oligosacharides in milk protect human infants from gastrointestinal bacteria?", *J. Nutr.*, May 1, 1997, pp. 980S–984S.
Cervantes et al., "Alpha 1–2 fucosylated chains (H–2 and Lewis b) are the main human milk receptor analogs for Campylobacter," *Pediatr. Res.*, 1995, vol. 37, p. 171A (abstract).
Masutani et al., "Purification and characterization of secretory–type GDP–L–fucose:beta–D–galactosidase 2–alpha–L–fucosyltransferase from human gastric mucosa," *J. Biochem (Tokyo)*, Sep. 1995, vol. 118, pp. 541–545.
Chandrasekaran et al., "Expression of blood group Lewis b determinant from Lewis a: association of this novel alpha (1,2)–L–fucosylating activity with the Lewis type alpha (1,3/4)–L–fucoslytransferase," *Biochemistry*, Apr. 11, 1995, vol. 34, pp. 4748–4756.
Larsen et al., "Molecular cloning, sequence, and expression of a human GDP–L–fucose–beta–D–galactosidase 2–alpha–L–fucosyltransferase cDNA that can form the H blood group antigen," *Proc. Natl. Acad. Sci. USA*, Sep. 1990, vol. 87, pp. 6674–6678.
Seiji Hitoshi et al., Molecular cloning and expression of a third type of rabbit GDP–L–fucose: β–D–Galactosidase 2–α–L–fucosyltransferase, *J. of Biol. Chem.*, 271(28):16975–16981 (1996).
Jing Sun et al., "Elevated expression of H type GDP–L–fucose: β–D–galactosidase α–2–L–fucosyltransferase is associated with human colon adenocarcinoma progression", *Proc. Natl. Acad. Sci., USA*, 92:5724–5728 (1995).
Armin Sepp et al., "Expression of α–1,3–Galactose and Other Type 2 Oligosacharaide Structures in a Porcine Endothelial Cell Line Transfected with Human α–1,2–Fucosyltranserase cDNA," *The Journal of Biol. Chemistry*, vol. 272, No. 37, 1997, pp. 23104–23110.

* cited by examiner

Primary Examiner—Ponnathapu Achutamurthy
Assistant Examiner—Christian L. Fronda
(74) Attorney, Agent, or Firm—Fish & Richardson P.C.

(57) ABSTRACT

A bacterial α1,2-fucosyltransferase gene and deduced amino acid sequence is provided. The gene is useful for preparing α1,2-fucosyltransferase polypeptide, and active fragment thereof, which can be used in the production of oligosaccharides such as Lewis X, Lewis Y, Lewis B and H type 1, which are structurally similar to certain tumor-associated carbohydrate antigens found in mammals. These product glycoconjugates also have research and diagnostic utility in the development of assays to detect mammalian tumors.

15 Claims, 8 Drawing Sheets

```
         HP 0095    0094   0093   0092 (hsdM)      26695

GW44 →            ← GW32

..........                ..........       UA802
                            fucT2
```

FIG. 1A

```
                          poly C tract
26695    TATATCCCCCTTTAATCAAGCAAACCTTCACTCTACCCCCCCCCGAAAA
                                                  xx
UA802  . TATATCCCTCTTTAATCAAGCAAACCTTCACTCTACCCCCCC--GAAAA imperfect TAA repeats              HP0094 stop ***
line 2   TAATAAGAATAATAATAAAAAAGAGGAAGAATATCAGTGCAAGTTTCTTTGATTTTAGC
                                  x                  x
         TAATAAAATAATAATAAAAAAGAGGAAGAATACCAGCGCAAGCTTTCTTTGATTTTAGC line 3   CGCTAAAAACAGGCGTGTTTGTGCATATAAGAAGAGGGGATTATGTGGGATTGGCTGTCA
                           x
         CGCTAAAAACAGGCGTATTTGTGCATATAAGAAGAGGGGATTATGTGGGATTGGCTGTCA ...start of HP0093
line 4   GCTTGGTATTGACTATCAAAAAAAGGCGCTTGAGTATATGGCAAAGCCGTGCCAAACAT
                    x
         GCTTGGTATTGATTATCAAAAAAAGGCGCTTGAGTATATGGCAAAGCCGTGCCAAACAT
                                          ***stop of -1 frame
```

FIG. 1B

```
gaacactcac acgcgtcttt ttcaaataaa aaattcaaat gatttgaaag cgttacccca   60
cttttaggc ttttattgaa aaagggcttt aaagttggct aaaataggcg ttttatttga  120
aaaacaaagg ggttga atg gct ttt aaa gtg gtg caa att tgt ggg ggg ctt 172
               Met Ala Phe Lys Val Val Gln Ile Cys Gly Gly Leu
                 1               5                  10
ggg aat caa atg ttt caa tac gct ttc gct aaa agt ttg caa aaa cac  220
Gly Asn Gln Met Phe Gln Tyr Ala Phe Ala Lys Ser Leu Gln Lys His
         15              20                  25
ctt aat acg ccc gta cta tta gac act act tct ttt gat tgg agc aat  268
Leu Asn Thr Pro Val Leu Leu Asp Thr Thr Ser Phe Asp Trp Ser Asn
     30                  35                  40
agg aaa atg caa tta gag ctt ttc cct att gat ttg ccc tat gcg aat  316
Arg Lys Met Gln Leu Glu Leu Phe Pro Ile Asp Leu Pro Tyr Ala Asn
45              50                  55                      60
gca aaa gaa atc gct ata gct aaa atg caa cat ctc ccc aag tta gta  364
Ala Lys Glu Ile Ala Ile Ala Lys Met Gln His Leu Pro Lys Leu Val
             65                  70                  75
aga gat gca ctc aaa tac ata gga ttt gat agg gtg agt caa gaa atc  412
Arg Asp Ala Leu Lys Tyr Ile Gly Phe Asp Arg Val Ser Gln Glu Ile
                 80                  85                  90
gtt ttt gaa tac gag cct aaa ttg tta aag cca agc cgt ttg act tat  460
Val Phe Glu Tyr Glu Pro Lys Leu Leu Lys Pro Ser Arg Leu Thr Tyr
             95                 100                 105
ttt ttt ggc tat ttc caa gat cca cga tat ttt gat gct ata tcc tct  508
Phe Phe Gly Tyr Phe Gln Asp Pro Arg Tyr Phe Asp Ala Ile Ser Ser
     110                 115                 120
tta atc aag caa acc ttc act cta ccc ccc ccc ccc gaa aat aat aaa  556
Leu Ile Lys Gln Thr Phe Thr Leu Pro Pro Pro Pro Glu Asn Asn Lys
125             130                 135                     140
aat aat aat aaa aaa gag gaa gaa tac cag cgc aag ctt tct ttg att  604
Asn Asn Asn Lys Lys Glu Glu Glu Tyr Gln Arg Lys Leu Ser Leu Ile
                145                 150                 155
tta gcc gct aaa aac agc gta ttt gtg cat ata aga aga ggg gat tat  652
Leu Ala Ala Lys Asn Ser Val Phe Val His Ile Arg Arg Gly Asp Tyr
             160                 165                 170
gtg ggg att ggc tgt cag ctt ggt att gat tat caa aaa aag gcg ctt  700
Val Gly Ile Gly Cys Gln Leu Gly Ile Asp Tyr Gln Lys Lys Ala Leu
         175                 180                 185
gag tat atg gca aag cgc gtg cca aac atg gag ctt ttt gtg ttt tgc  748
Glu Tyr Met Ala Lys Arg Val Pro Asn Met Glu Leu Phe Val Phe Cys
     190                 195                 200
gaa gac tta aaa ttc acg caa aat ctt gat ctt ggc tac cct ttc acg  796
Glu Asp Leu Lys Phe Thr Gln Asn Leu Asp Leu Gly Tyr Pro Phe Thr
205             210                 215                     220
gac atg acc act agg gat aaa gaa gaa gag gcg tat tgg gat atg ctg  844
Asp Met Thr Thr Arg Asp Lys Glu Glu Glu Ala Tyr Trp Asp Met Leu
                225                 230                 235
ctc atg caa tct tgc aag cat ggc att atc gct aat agc act tat agc  892
Leu Met Gln Ser Cys Lys His Gly Ile Ile Ala Asn Ser Thr Tyr Ser
             240                 245                 250
tgg tgg gcg gct tat ttg atg gaa aat cca gaa aaa atc att att ggc  940
Trp Trp Ala Ala Tyr Leu Met Glu Asn Pro Glu Lys Ile Ile Ile Gly
         255                 260                 265
ccc aaa cac tgg ctt ttt ggg cat gaa aat att ctt tgt aag gaa tgg  988
Pro Lys His Trp Leu Phe Gly His Glu Asn Ile Leu Cys Lys Glu Trp
     270                 275                 280
gtg aaa ata gaa tcc cat ttt gag gta aaa tcc caa aaa tat aac gct 1036
Val Lys Ile Glu Ser His Phe Glu Val Lys Ser Gln Lys Tyr Asn Ala
285             290                 295                     300
taaagcggct taaaaaaagg gcttactaga ggtttaatct ttgattttag atcggatttc 1096
tttatagcga gcgtctaatt cta                                       1119
```

FIG. 1D

| | Motif I | | Motif II | | Motif III | |
|---|---|---|---|---|---|---|
| man Fut1 (365 aa) | GRFGNQMGQYA | (87-97) | VGVHVRRGDYL | (215-225) | GTFGFWAAYL | (308-317) |
| man Fut2 (343 aa) | GRLGNQMGEYA | (70-80) | VGVHVRRGDYV | (196-206) | GTFGIWAAYL | (289-298) |
| Hp FucT2 (300 aa) | GGLGNQMFQYA | (10-20) | VFVHIRRGDYV | (163-173) | STYSWWAAYL | (249-258) |
| Ye WbcH (283 aa) | GGLGNQLFQVA | (9-19) | VGIHIRRGDFV | (158-168) | STFSWWAAIL | (241-250) |
| Ll EpsII (309 aa) | GNLGNQLFIYA | (8-18) | ICVSIRRGDYV | (173-183) | SSFSWWTEFL | (263-272) |

SEQUENCE LISTING

<160> NUMBER OF SEQ ID NOS: 23

<210> SEQ ID NO 1
<211> LENGTH: 1119
<212> TYPE: DNA
<213> ORGANISM: Helicobacter pylori
<220> FEATURE:
<221> NAME/KEY: CDS
<222> LOCATION: (137)...(1036)

<400> SEQUENCE: 1

```
gaacactcac acgcgtcttt ttcaaataaa aaattcaaat gatttgaaag cgttacccca      60 cttttttaggc ttttattgaa aaagggcttt aaagttggct aaaataggcg tttttatttga    120 aaaacaaagg ggttga atg gct ttt aaa gtg gtg caa att tgt ggg ggg ctt      172
              Met Ala Phe Lys Val Val Gln Ile Cys Gly Gly Leu
                1               5                   10 ggg aat caa atg ttt caa tac gct ttc gct aaa agt ttg caa aaa cac        220
Gly Asn Gln Met Phe Gln Tyr Ala Phe Ala Lys Ser Leu Gln Lys His
        15                  20                  25 ctt aat acg ccc gtg cta tta gac act act tct ttt gat tgg agc aat        268
Leu Asn Thr Pro Val Leu Leu Asp Thr Thr Ser Phe Asp Trp Ser Asn
    30                  35                  40 agg aaa atg caa tta gag ctt ttc cct att gat ttg ccc tat gcg aat        316
Arg Lys Met Gln Leu Glu Leu Phe Pro Ile Asp Leu Pro Tyr Ala Asn
45                  50                  55                  60 gca aaa gaa atc gct ata gct aaa atg caa cat ctc ccc aag tta gta        364
```

```
Ala Lys Glu Ile Ala Ile Ala Lys Met Gln His Leu Pro Lys Leu Val
                65                  70                  75 aga gat gca ctc aaa tac ata gga ttt gat agg gtg agt caa gaa atc      412
Arg Asp Ala Leu Lys Tyr Ile Gly Phe Asp Arg Val Ser Gln Glu Ile
                80                  85                  90 gtt ttt gaa tac gag cct aaa ttg tta aag cca agc cgt ttg act tat      460
Val Phe Glu Tyr Glu Pro Lys Leu Leu Lys Pro Ser Arg Leu Thr Tyr
            95                 100                 105 ttt ttt ggc tat ttc caa gat cca cga tat ttt gat gct ata tcc tct      508
Phe Phe Gly Tyr Phe Gln Asp Pro Arg Tyr Phe Asp Ala Ile Ser Ser
        110                 115                 120 tta atc aag caa acc ttc act cta ccc ccc ccc ccc gaa aat aat aaa      556
Leu Ile Lys Gln Thr Phe Thr Leu Pro Pro Pro Pro Glu Asn Asn Lys
125                 130                 135                 140 aat aat aat aaa aaa gag gaa gaa tac cag cgc aag ctt tct ttg att      604
Asn Asn Asn Lys Lys Glu Glu Glu Tyr Gln Arg Lys Leu Ser Leu Ile
                145                 150                 155 tta gcc gct aaa aac agc gta ttt gtg cat ata aga aga ggg gat tat      652
Leu Ala Ala Lys Asn Ser Val Phe Val His Ile Arg Arg Gly Asp Tyr
                160                 165                 170 gtg ggg att ggc tgt cag ctt ggt att gat tat caa aaa aag gcg ctt      700
Val Gly Ile Gly Cys Gln Leu Gly Ile Asp Tyr Gln Lys Lys Ala Leu
            175                 180                 185 gag tat atg gca aag cgc gtg cca aac atg gag ctt ttt gtg ttt tgc      748
Glu Tyr Met Ala Lys Arg Val Pro Asn Met Glu Leu Phe Val Phe Cys
        190                 195                 200 gaa gac tta aaa ttc acg caa aat ctt gat ctt ggc tac cct ttc acg      796
Glu Asp Leu Lys Phe Thr Gln Asn Leu Asp Leu Gly Tyr Pro Phe Thr
205                 210                 215                 220 gac atg acc act agg gat aaa gaa gaa gag gcg tat tgg gat atg ctg      844
Asp Met Thr Thr Arg Asp Lys Glu Glu Glu Ala Tyr Trp Asp Met Leu
                225                 230                 235 ctc atg caa tct tgc aag cat ggc att atc gct aat agc act tat agc      892
Leu Met Gln Ser Cys Lys His Gly Ile Ile Ala Asn Ser Thr Tyr Ser
                240                 245                 250 tgg tgg gcg gct tat ttg atg gaa aat cca gaa aaa atc att att ggc      940
Trp Trp Ala Ala Tyr Leu Met Glu Asn Pro Glu Lys Ile Ile Ile Gly
            255                 260                 265 ccc aaa cac tgg ctt ttt ggg cat gaa aat att ctt tgt aag gaa tgg      988
Pro Lys His Trp Leu Phe Gly His Glu Asn Ile Leu Cys Lys Glu Trp
        270                 275                 280 gtg aaa ata gaa tcc cat ttt gag gta aaa tcc caa aaa tat aac gct     1036
Val Lys Ile Glu Ser His Phe Glu Val Lys Ser Gln Lys Tyr Asn Ala
285                 290                 295                 300 taaagcggct taaaaaagg gcttactaga ggtttaatct ttgattttag atcggatttc    1096
tttatagcga gcgtctaatt cta                                           1119

<210> SEQ ID NO 2
<211> LENGTH: 300
<212> TYPE: PRT
<213> ORGANISM: Helicobacter pylori

<400> SEQUENCE: 2

Met Ala Phe Lys Val Val Gln Ile Cys Gly Gly Leu Gly Asn Gln Met
1               5                   10                  15

Phe Gln Tyr Ala Phe Ala Lys Ser Leu Gln Lys His Leu Asn Thr Pro
                20                  25                  30

Val Leu Leu Asp Thr Thr Ser Phe Asp Trp Ser Asn Arg Lys Met Gln
            35                  40                  45
```

```
Leu Glu Leu Phe Pro Ile Asp Leu Pro Tyr Ala Asn Ala Lys Glu Ile
 50                  55                  60

Ala Ile Ala Lys Met Gln His Leu Pro Lys Leu Val Arg Asp Ala Leu
 65                  70                  75                  80

Lys Tyr Ile Gly Phe Asp Arg Val Ser Gln Glu Ile Val Phe Glu Tyr
                 85                  90                  95

Glu Pro Lys Leu Leu Lys Pro Ser Arg Leu Thr Tyr Phe Phe Gly Tyr
                100                 105                 110

Phe Gln Asp Pro Arg Tyr Phe Asp Ala Ile Ser Ser Leu Ile Lys Gln
                115                 120                 125

Thr Phe Thr Leu Pro Pro Pro Glu Asn Asn Lys Asn Asn Asn Lys
                130                 135                 140

Lys Glu Glu Glu Tyr Gln Arg Lys Leu Ser Leu Ile Leu Ala Ala Lys
145                 150                 155                 160

Asn Ser Val Phe Val His Ile Arg Arg Gly Asp Tyr Val Gly Ile Gly
                165                 170                 175

Cys Gln Leu Gly Ile Asp Tyr Gln Lys Lys Ala Leu Glu Tyr Met Ala
                180                 185                 190

Lys Arg Val Pro Asn Met Glu Leu Phe Val Phe Cys Glu Asp Leu Lys
                195                 200                 205

Phe Thr Gln Asn Leu Asp Leu Gly Tyr Pro Phe Thr Asp Met Thr Thr
210                 215                 220

Arg Asp Lys Glu Glu Ala Tyr Trp Asp Met Leu Met Gln Ser
225                 230                 235                 240

Cys Lys His Gly Ile Ile Ala Asn Ser Thr Tyr Ser Trp Trp Ala Ala
                245                 250                 255

Tyr Leu Met Glu Asn Pro Glu Lys Ile Ile Ile Gly Pro Lys His Trp
                260                 265                 270

Leu Phe Gly His Glu Asn Ile Leu Cys Lys Glu Trp Val Lys Ile Glu
                275                 280                 285

Ser His Phe Glu Val Lys Ser Gln Lys Tyr Asn Ala
                290                 295                 300

<210> SEQ ID NO 3
<211> LENGTH: 19
<212> TYPE: DNA
<213> ORGANISM: Artificial Sequence
<220> FEATURE:
<223> OTHER INFORMATION: synthetically generated oligonucleotide

<400> SEQUENCE: 3
gaacactcac acgcgtctt                                              19

<210> SEQ ID NO 4
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 4
tagaattaga cgctcgctat                                             20

<210> SEQ ID NO 5
<211> LENGTH: 19
<212> TYPE: DNA
<213> ORGANISM: Artificial Sequence
<220> FEATURE:
```

<223> OTHER INFORMATION: synthetically generated oligonucleotide

<400> SEQUENCE: 5
cggagggctt gggaatcaa                                                    19

<210> SEQ ID NO 6
<211> LENGTH: 231
<212> TYPE: DNA
<213> ORGANISM: Helicobacter pylori

<400> SEQUENCE: 6
tatatcccct taatcaagc aaaccttcac tctacccccc cccccccga aaataataag        60 aataataata aaaagagga agaatatcag tgcaagcttt ctttgattt agccgctaaa       120 aacagcgtgt ttgtgcatat aagaagaggg gattatgtgg ggattggctg tcagcttggt    180
attgactatc aaaaaaggc gcttgagtat atggcaaagc gtgccaaaca t               231

<210> SEQ ID NO 7
<211> LENGTH: 230
<212> TYPE: DNA
<213> ORGANISM: Helicobacter pylori

<400> SEQUENCE: 7
tatatcctct taatcaagc aaaccttcac tctacccccc ccccccgaaa ataataaaaa       60
taataataaa aaagaggaag aataccagcg caagctttct ttgattttag ccgctaaaaa    120
cagcgtattt gtgcatataa gaagagggga ttatgtggga ttggctgtca gcttggtatt    180
gattatcaaa aaaggcgct tgagtatatg gcaaagcgcg tgccaaacat               230

<210> SEQ ID NO 8
<211> LENGTH: 60
<212> TYPE: RNA
<213> ORGANISM: Helicobacter pylori

<400> SEQUENCE: 8
uaauaagaau aauaauaaaa aagaggaaga auaucagugc aagcuuucuu ugauuuuagc    60

<210> SEQ ID NO 9
<211> LENGTH: 11
<212> TYPE: PRT
<213> ORGANISM: Homo sapiens

<400> SEQUENCE: 9

Gly Arg Phe Gly Asn Gln Met Gly Gln Tyr Ala
 1               5                  10

<210> SEQ ID NO 10
<211> LENGTH: 11
<212> TYPE: PRT
<213> ORGANISM: Homo sapiens

<400> SEQUENCE: 10

Gly Arg Leu Gly Asn Gln Met Gly Glu Tyr Ala
 1               5                  10

<210> SEQ ID NO 11
<211> LENGTH: 11
<212> TYPE: PRT
<213> ORGANISM: Helicobacter pylori

<400> SEQUENCE: 11

Gly Gly Leu Gly Asn Gln Met Phe Gln Tyr Ala

```
1               5              10

<210> SEQ ID NO 12
<211> LENGTH: 11
<212> TYPE: PRT
<213> ORGANISM: Yersinia enterocolitica

<400> SEQUENCE: 12

Gly Gly Leu Gly Asn Gln Leu Phe Gln Val Ala
1               5              10

<210> SEQ ID NO 13
<211> LENGTH: 11
<212> TYPE: PRT
<213> ORGANISM: Lactococcus lactis

<400> SEQUENCE: 13

Gly Asn Leu Gly Asn Gln Leu Phe Ile Tyr Ala
1               5              10

<210> SEQ ID NO 14
<211> LENGTH: 11
<212> TYPE: PRT
<213> ORGANISM: Homo sapiens

<400> SEQUENCE: 14

Val Gly Val His Val Arg Arg Gly Asp Tyr Leu
1               5              10

<210> SEQ ID NO 15
<211> LENGTH: 11
<212> TYPE: PRT
<213> ORGANISM: Homo sapiens

<400> SEQUENCE: 15

Val Gly Val His Val Arg Arg Gly Asp Tyr Val
1               5              10

<210> SEQ ID NO 16
<211> LENGTH: 11
<212> TYPE: PRT
<213> ORGANISM: Helicobacter pylori

<400> SEQUENCE: 16

Val Phe Val His Ile Arg Arg Gly Asp Tyr Val
1               5              10

<210> SEQ ID NO 17
<211> LENGTH: 11
<212> TYPE: PRT
<213> ORGANISM: Yersinia enterocolitica

<400> SEQUENCE: 17

Val Gly Ile His Ile Arg Arg Gly Asp Phe Val
1               5              10

<210> SEQ ID NO 18
<211> LENGTH: 11
<212> TYPE: PRT
<213> ORGANISM: Lactococcus lactis

<400> SEQUENCE: 18

Ile Cys Val Ser Ile Arg Arg Gly Asp Tyr Val
1               5              10
```

```
<210> SEQ ID NO 19
<211> LENGTH: 10
<212> TYPE: PRT
<213> ORGANISM: Homo sapiens

<400> SEQUENCE: 19

Gly Thr Phe Gly Phe Trp Ala Ala Tyr Leu
 1               5                  10

<210> SEQ ID NO 20
<211> LENGTH: 10
<212> TYPE: PRT
<213> ORGANISM: Homo sapiens

<400> SEQUENCE: 20

Gly Thr Phe Gly Ile Trp Ala Ala Tyr Leu
 1               5                  10

<210> SEQ ID NO 21
<211> LENGTH: 10
<212> TYPE: PRT
<213> ORGANISM: Helicobacter pylori

<400> SEQUENCE: 21

Ser Thr Tyr Ser Trp Trp Ala Ala Tyr Leu
 1               5                  10

<210> SEQ ID NO 22
<211> LENGTH: 10
<212> TYPE: PRT
<213> ORGANISM: Yersinia enterocolitica

<400> SEQUENCE: 22

Ser Thr Phe Ser Trp Trp Ala Ala Ile Leu
 1               5                  10

<210> SEQ ID NO 23
<211> LENGTH: 10
<212> TYPE: PRT
<213> ORGANISM: Lactococcus lactis

<400> SEQUENCE: 23

Ser Ser Phe Ser Trp Trp Thr Glu Phe Leu
 1               5                  10
```

…# α1,2-FUCOSYLTRANSFERASE

CROSS REFERENCE TO RELATED APPLICATIONS

This application is a Divisional of application Ser. No. 09/433,598, filed Nov. 2, 1999, now U.S. Pat. No. 6,238,894, which claims priority under 35 U.S.C. Section 119(e) to provisional patent application No. 60/107,268, filed on Nov. 4, 1998, each of which is herein incorporated by reference.

FIELD OF THE INVENTION

The present invention relates generally to the field of α1,2-fucosyltransferases and, more specifically, to α1,2-fucosyltransferase polypeptides.

BACKGROUND OF THE INVENTION

*Helicobacter pylori* is an important human pathogen which causes both gastric and duodenal ulcers and has also been associated with gastric cancer and lymphoma. This microorganism has been shown to express cell surface glycoconjugates including Lewis X, Lewis Y, and sialyl Lewis X. These bacterial oligosaccharides are structurally similar to tumor-associated carbohydrate antigens found in mammals.

The presence of *H. pylori* isolate has been associated with an increased risk for development of gastric cancer (Wirth, H. -P., Yang, M., Karita, M., and Blaser, M. J. (1996) *Infect. Immun.* 64, 4598–4605). This pathogen is highly adapted to colonize human gastric mucosa and may remain in the stomach with or without causing symptoms for many years. Although *H. pylori* elicits local as well as systemic antibody responses, it escapes elimination by the host immune response due to its sequestered habitation within human gastric mucosa. Another mechanism by which *H. pylori* may protect itself from the action of the host immune response is the production of surface antigens mimicking those in the host.

In mammalian cells the enzyme fucosyltransferase (namely FucT) catalyzes the last step in the synthesis of two carbohydrate structures, Galβ 1–4[Fucα1–3] GlcNAc (Lewis X, $Le^x$ for short) or NeuAcα2–3-Galβ 1–4[Fucα1–3] GlcNAc (sialyl Lewis X, $sLe^x$ for short). (Lowe et al., 1990, Cell 57: 475–484.; Kukowska-Latallo et al., 1990, Genes & Development 4:1288–1303.) Cell surface α(1,3)- and α(1,2)-fucosylated oligosaccharides, that is, Lewis X ($Le^x$), sialyl Lewis X ($sLe^x$) and Lewis Y ($Le^y$), are present on both eukaryotic and microbial cell surfaces. In mammals, $Le^x$ is a stage-specific embryonic antigen, however, $Le^x$, $sLe^x$ and $Le^y$ are also regarded as tumor-associated markers. The biological functions of these bacterial oligosaccharide structures are not fully understood. It has been suggested that such glycoconjugates produced by *H. pylori*, may mimic host cell antigens and could mask the bacterium from the host immune response. It is also possible that these bacterial Lewis antigens could down regulate the host T-cell response. Therefore, production of such antigens may contribute to colonization and long-term infection of the stomach by *H. pylori*.

Presently, use of carbohydrates as potential therapeutic drugs has become popular in the field of medical chemistry. In addition, qualitative and quantitative carbohydrates including $Le^x$, $Le^y$ and $sLe^x$ are also required as reagents for assaying the enzymes which are involved in the biosynthesis of glycoconjugates in cells. $Le^x$, $Le^y$ and $sLe^x$ products which are commercially available are chemically synthesized. However, synthesis of these products gives rise to several limitations such as time-consuming, complicated procedures and low yields. Although several mammalian fucosyltransferases have been cloned and expressed, enzymatic synthesis of $Le^x$, $Le^y$ and $sLe^x$ products for a commercial purpose has not been reported.

The whole genome sequence of *H. pylori* 26695 had been published, which will undoubtedly facilitate the genetic studies of *H. pylori*. *H. pylori* genome sequence revealed the existence of two copies of α(1,3) fucT gene, whereas no putative α(1,2) fucT gene had been annotated.

SUMMARY OF THE INVENTION

The present invention is based on the discovery of a α1,2-fucosyltransferase polypeptide and gene which encodes the polypeptide. The gene was expressed in vitro and a mutagenesis study demonstrated that this gene is involved in $Le^y$ synthesis. The present invention includes a polynucleotide sequence encoding α1,2-fucosyltransferase polypeptide which is useful in the detection and synthesis of α1,2-fucosyltransferase polypeptide, and an α1,2-fucosyltransferase that is able to synthesize $Le^Y$, $Le^B$ and H type 1 structures.

*Helicobacter pylori* lipopolysaccharide (LPS) express human oncofetal antigens Lewis X and Lewis Y. The synthesis of Lewis Y involves the actions of α(1,3) and α(1,2) fucosyltransferases (FucTs). Disclosed herein are the molecular cloning and characterization of genes encoding *H. pylori* α(1,2) FucT (Hp fucT2) from various *H. pylori* strains. Also provided are constructed Hp fucT2 knock-out mutants that demonstrate the loss of Lewis Y production in these mutants by ELISA and immunoelectron microscopy. The α1,2 fucT2 gene contains a hypermutable sequence (poly C and TAA repeats) which provides a possibility of frequent shifting into and out of coding frame by a polymerase slippage mechanism. Thus, α1,2fucT2 gene displays two major genotypes: either encoding a single full-length open reading frame (ORF, as in the strain UA802), or truncated ORFs (as in the strain 26695). In vitro expression of Hp fucT2 genes demonstrated that both types of the gene have a potential to produce the full-length protein. The production of the fill-length protein by the 26695 fucT2 gene could be attributed to translational—1 frameshifting, since a perfect translation frameshift cassette resembling that of *Escherichia coli* dnaX gene is present. The examination of the strain UA1174 revealed that its fucT2 gene has a frameshifted ORF at the DNA level which cannot be compensated by translation frameshifting, accounting for its Lewis Y -off phenotype. In another strain, UA1218, the fucT2 gene is turned off apparently due to the loss of its promoter. Based on these data, we proposed a model for the variable expression of Lewis Y by *H. pylori*, in which the regulation at the level of replication, transcription, and translation of the fucT2 gene may all be involved.

In another embodiment, the invention provides a method of using the novel α1,2-fucosyltransferase to synthesize oligosaccharides such as $Le^x$, $Le^y$, $sLe^x$, $Le^A$, $Le^B$, H type 1 and H type 2.

In another embodiment the invention provides the novel polypeptide of α1,2-fucosyltransferase which is useful in the development of antibodies to α1,2-fucosyltransferase.

In another embodiment, a polypeptide of α1,2-fucosyltransferase having a frameshift variant resulting from a "slippery" heptanucleic acid sequence X XXY YYZ, wherein X=C or A, Y=T or A and Z=A or G (e.g., A AA A AG) is provided. In another embodiment, the α1,2-fucosyltransferase is a polypeptide which has a sequence of SEQ ID NO:2. In another embodiment the polynucleotide sequence encoding α1,2-fucosyltransferase has a variable number of poly-cytosine repeats and TAA repeats in different H. pylori strains.

Further provided is a method for producing α1,2-fucosyltransferase. The method involves the step of culturing a gene expression system which comprises a host cell which has been recombinantly modified with a polynucleotide encoding α1,2-fucosyltransferase or a portion thereof and harvesting the α1,2-fucosyltransferase. A preferred embodiment of the method is directed to the use of the claimed genetic expression system which produces α1,2-fucosyltransferase.

Further provided is a method to measure the enzymatic activity and acceptor specificity of α1,2-fucosyltransferase. The method involves the use of a structurally defined oligosaccharide substrate (acceptor) in a radioactive labeled assay system and identification of the reaction products by capillary electrophoresis. In another embodiment, an α1,2-fucosyltransferase has a substrate specificity that is distinct from the conventional α1,2-fucosyltransferase of mammalian origin and uses a different pathway to synthesize Lewis antigens.

Also provided are knockout organisms in which expression of α1,2-fucosyltransferase has been prevented or in which the α1,2-fucosyltransferase expression results in a polypeptide lacking wild type biological activity.

These and many other features and attendant advantages of the present invention will become better understood by reference to the following detailed description of the invention when taken in conjunction with the Examples.

ABBREVIATIONS

The abbreviation used are: α1,2-FucT, α1,2-fucosyltransferase unless specified otherwise; $Le^x$, Lewis X; $sLe^x$, sialyl-Lewis X; Le Y, Lewis Y; $Le^B$, Lewis B; nt, nucleotide (s); kb, kilobase (s); aa, amino acid (s); PCR, polymerase chain reaction; ORF, open reading frame; RSB, a ribosomal binding site; LPS, lipopolysaccharides; LacNAc-R, Galβ1–4GlcNAcβ-O-(CH$_2$)$_8$COOMe;Galβ1–3GlcNAc-R, Galβ1–3GlcNAcb-O-(CH$^2$)$^8$ COOMe; LacNAc-TMR, Galβ1,4GlcNAcβ-O-(CH$_2$)$_8$CO-NHCH$_2$CH$_2$NH-TMR.

DETAILED DESCRIPTION OF THE INVENTION

Figure 1C:
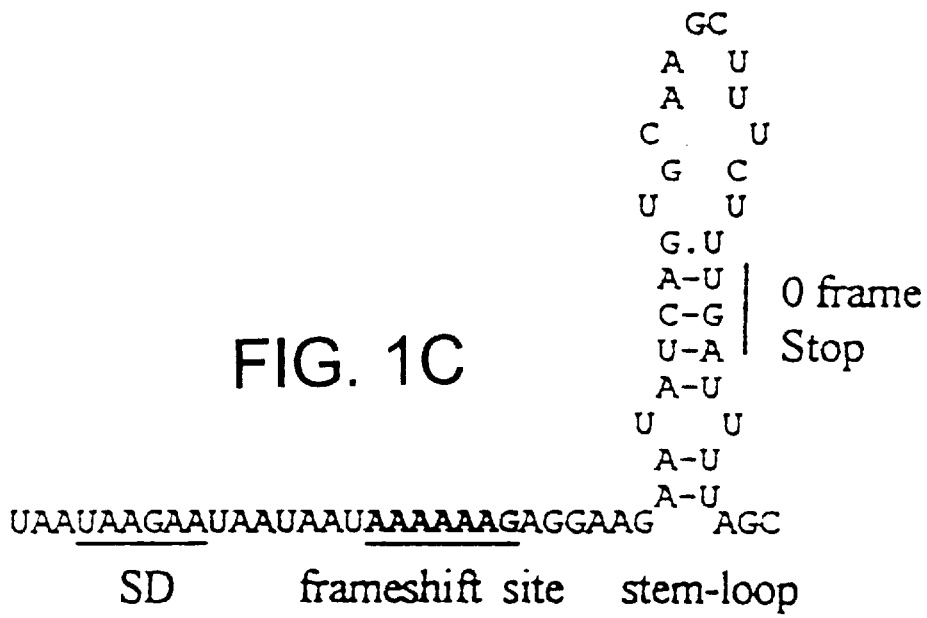
FIG. 1 shows the nucleotide sequence analysis of Hp fucT2. (A) Gene organization of Hp fucT2 region in the genome of H. pylori 26695 and UA802. GW44 and GW32 indicate the two primers used for cloning Hp fucT2 genes. (B) Nucleotide sequences of the center region of Hp fucT2 showing the features (simple repeats) responsible for frameshift between prototype (UA802; SEQ ID NO:7) and variant type (26695; SEQ ID NO:6) genes. The divergent nucleotides between the two sequences are marked by "x". Due to the different repeat number of poly C residues, the initiating reading frame of 26695 fucT2 (HP0094) encounters a TGA stop codon (marked with asterisks) shortly after the poly-C region. About 110 bp further downstream, there appears a potential start codon ATG (marked with dots) in the −1 frame (HP0093), which is the same as the reading frame of 802 fucT2. The three putative X XXY YYZ motifs (X, Y, and Z represent specific nucleotides in a particular reading from) are given in bold face and underlined. Additional elements for programmed translation frameshift in 26695 fucT2 resembling those in E. coli dnaX gene are also underlined. (C) The putative 26695 fucT2 translation frameshift cassette. Shown is the mRNA structure (SEQ ID NO:8) deduced from the DNA sequence in line 2 of (B). The AAAAAAG heptamer (bold) is a highly slippery sequence identified in other DNA sequences. UGA (sidelined in the stem structure) is the stop codon in the initiating frame (0 frame). SD indicates an internal Shine-Dalgarno-like sequence. According to the E. coli dnaX frameshift model, AAAAAAG sequence is the frameshift site, and both upstream SD sequence and downstream stem-loop structure enhance frameshifting. (D) Shows the amino acid sequence and nucleic acid sequence for α1,2 fucosyltransferase (SEQ ID NOs:2 and 1, respectively).

The present invention relates to a purified α1,2-fucosyltransferase polypeptide, polynucleotide which encode the α1,2-fucosyltransferase, and the use of the α1,2-fucosyltransferase gene and α1,2-fucosyltransferase polypeptide in the production of biologics and in the screening of biological tissues and fluids. The invention also relates to antibodies against α1,2-fucosyltransferase polypeptides and their use in diagnosing disorders and in monitoring disease.

The α1,2-fucosyltransferase Polypeptide

The amino acid sequence encoded by the α1,2-fucosyltransferase gene is shown in FIG. 1D (SEQ ID NO:2). Because the α1,2-fucosyltransferase are prokaryotically derived post-translational modifications are not made to the enzyme, unlike the eukaryotically expressed α1,2-fucosyltransferase.

Additionally, the α1,2-fucosyltransferase polypeptide may be altered by addition, substitution or deletions of peptide sequences in order to modify its activity. For example, polypeptide sequences may be fused to the α1,2-fucosyltransferase polypeptide in order to effectuate additional enzymatic activity. Alternatively, amino acids may be deleted or substituted to remove or modify the activity of the protein. The protein may be modified to lack α1,2-fucosyltransferase enzymatic activity, but retain its three-dimensional structure. Such modification would be useful in the development of antibodies against α1,2-fucosyltransferase polypeptide as described more fully below.

In yet another embodiment, the invention includes aspects of the enzymatic activity of α1,2-fucosyltransferase, wherein the α1,2-fucosyltransferase polypeptide lacks α1,4-fucosyltransferase or α1,3-fucosyltransferase activity or lacks both α1,3-fucosyltransferase and α1,4-fucosyltransferase activity.

The α1,2-fucosyltransferase gene product may include those polypeptides encoded by the α1,2-fucosyltransferase gene sequences described in the section below. Specifically, α1,2-fucosyltransferase gene products, sometimes referred to herein as "α1,2-fucosyltransferase polypeptide" may include α1,2-fucosyltransferase gene product encoded by an α1,2-fucosyltransferase gene sequence shown in FIG. 1 and SEQ ID NO:1, as well as different versions of the gene sequences deposited in GenBank under the accession numbers AF093828–AF093833. Thus, the term "α1,2-fucosyltransferase polypeptide" includes full length expression as well as polypeptides, such as smaller peptides, which retain a biological activity of the full length product, such as α1,2-fucosyltransferase activity.

In addition, α1,2-fucosyltransferase gene products may include proteins or polypeptides that represent functionally equivalent gene products. Such an equivalent α1,2-fucosyltransferase gene product may contain deletions, additions or substitutions of amino acid residues within the amino acid sequence encoded by the α1,2-fucosyltransferase gene sequences described above, but which results in a silent change, thus producing a functionally equivalent α1,2-fucosyltransferase gene product. Amino acid substitutions may be made on the basis of similarity in polarity, charge, solubility, hydrophobicity, hydrophilicity, and/or the amphipathic nature of the residues involved.

For example, nonpolar (hydrophobic) amino acids include alanine, leucine, isoleucine, valine, proline, phenylalanine, tryptophan, and methionine; planar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Functionally equivalent"as utilized herein, refers to a polypeptide capable of exhibiting a substantially similar in vivo activity as the endogenous α1,2-fucosyltransferase gene products encoded by the α1,2-fucosyltransferase gene sequences described above, as judged by any of a number of criteria, including but not limited to antigenicity, i.e., the ability to bind to an anti-α1, 2-fucosyltransferase antibody, immunogenicity, i.e., the ability to generate an antibody which is capable of binding a α1,2-fucosyltransferase protein or polypeptide, as well as enzymatic activity. For example, the frameshift mutant resulting from expression of the sequence XXXYYYZ results in a product which may retain antigenic properties similar to those of wild type α1,2-fucosyltransferase.

A substantially purified α1,2-fucosyltransferase protein, polypeptide, and derivative (including a fragment) is substantially free of other proteins, lipids, carbohydrates, nucleic acids, and other biological materials with which it is naturally associated. For example, a substantially purified functional fragment of α1,2-fucosyltransferase polypeptide can be at least 60%, by dry weight, the molecule of interest. One skilled in the art can purify a functional fragment of α1,2-fucosyltransferase protein using standard protein purification methods and the purity of the polypeptides can be determined using standard methods including, e.g., polyacrylamide gel electrophoresis (e.g., SDS-PAGE), column chromatography (e.g., high performance liquid chromatography), and amino-terminal amino acid sequence analysis.

Included within the scope of the invention are α1,2-fucosyltransferase proteins, polypeptides, and derivatives (including fragments) which are differentially modified during or after translation. Any of numerous chemical modifications may be carried out by known techniques, including but not limited to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc. Additionally, the composition of the invention may be conjugated to other molecules to increase their water-solubility (e.g., polyethylene glycol), half-life, or ability to bind targeted tissue.

Furthermore, nonclassical amino acids or chemical amino acid analogs can be introduced as a substitution or addition into the α1,2-fucosyltransferase polypeptide sequence. Nonclassical amino acids include, but are not limited to, the D-isomer of the common amino acids, α-amino isobutyric acid, 4-aminobutyric acid, Abu, 2-amino butyric acid, γ-Abu, epsilon-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids, such as β-methyl amino acids, α-methyl amino acids, Nα-methyl amino acids, and amino acid analogs in general. Furthermore, the amino acid can be D (dextrorotary) or L (levorotary).

While random mutations can be made to α1,2-fucosyltransferase DNA (using random mutagenesis techniques known to those skilled in the art) and the resulting mutant α1,2-fucosyltransferase polypeptides tested for activity, site-directed mutation of the α1,2-fucosyltransferase coding sequence can be engineered (using site-directed mutagenesis techniques well known to those skilled in the art) to create mutant α1,2-fucosyltransferase polypeptides with increased functional characteristics.

Polypeptides corresponding to one or more domains of the α1,2-fucosyltransferase protein, truncated or deleted α1,2-fucosyltransferase proteins, as well as fusion proteins in which the full length α1,2-fucosyltransferase proteins, polypeptides, or derivatives (including fragments), or truncated α1,2-fucosyltransferase, is fused to an unrelated protein, are also within the scope of the invention and can be designed on the basis of the α1,2-fucosyltransferase nucleotide and α1,2-fucosyltransferase amino acid sequences disclosed in this section and the section above. The fusion protein may also be engineered to contain a cleavage site located between a α1,2-fucosyltransferase sequence and the non-α1,2-fucosyltransferase protein sequence, so that the α1,2-fucosyltransferase polypeptide may be cleaved away from the non-α1,2-fucosyltransferase moiety. Such fusion proteins or polypeptides include but are not limited to IgFc fusion which may stabilize the α1,2-fucosyltransferase protein in vivo; or fusion to an enzyme, fluorescent protein, or luminescent protein which provide a marker function.

The α1,2-fucosyltransferase polypeptide may be produced by recombinant DNA technology using techniques well known in the art. Thus, methods for preparing the α1,2-fucosyltransferase polypeptides of the invention by expressing a nucleic acid containing α1,2-fucosyltransferase gene sequences are described herein. Methods which are well known to those skilled in the art can be used to construct expression vectors containing α1,2-fucosyltransferase coding sequences and appropriate transcriptional and translational control signals. These methods include, for example, in vitro recombinant DNA techniques, synthetic techniques, and in vivo genetic recombination. See, for example, the techniques described in Sambrook et al., 1989, *Molecular Cloning, a Laboratory Manual,* Cold Springs Harbor Press, N.Y., and Ausubel F. M. et al., eds., 1989, *Current Protocols in Molecular Biology,* Vol. 1, Green Publishing Associates, Inc., and John Willey & Sons, Inc., New York. Alternatively, RNA capable of encoding α1,2-fucosyltransferase polypeptide may be chemically synthesized using, for example, synthesizers. See, for example, the techniques described in "Oligonucleotide Synthesis" 1984, Gait, M. J. ed., IRL Press, Oxford, which is incorporated by reference herein in its entirety. The use of such synthetic peptide fragments of α1,2-fucosyltransferase for generating polyclonal antibodies is described below.

The α1,2-fucosyltransferase Gene

The α1,2-fucosyltransferase gene (FIG. 1) is expressed in *H. pylori*. Nucleic acid sequences of the identified α1,2-fucosyltransferase genes are described herein. As used herein, "α1,2-fucosyltransferase gene" refers to (a) a gene containing the DNA sequence shown in FIG. 1; (b) any DNA sequence that encodes the amino acid sequence shown in FIG. 1D, SEQ ID NO:2; (c) any DNA sequence that hybridizes to the complement of the coding sequences shown in FIG. 1, SEQ ID NO: 1, under stringent conditions, e.g., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel F. M. et al., eds., 1989, *Current Protocols in Molecular Biology,* Vol. 1, Green Publishing Associates, Inc., and John Willey & Sons, Inc., New York, at p. 2.10.3) and encodes a gene product functionally equivalent to a gene product encoded by sequences shown in FIG. 1; and/or (d) any DNA sequence that hybridizes to the complement of the coding sequences disclosed herein (as shown in FIG. 1), under less stringent conditions, such as moderately stringent conditions, e.g., washing in 0.2% SSC/0.1% SDS at 42° C. (Ausubel et al., 1989, supra), and encodes a gene product functionally equivalent to a gene product encoded by sequences shown in FIG. 1.

The invention also includes nucleic acid molecules, preferably DNA molecules, that hybridize to, and are therefore the complements of, the DNA sequences (a) through (c), in the preceding paragraph. Such hybridization conditions may be highly stringent or less highly stringent, as described above. In instances wherein the nucleic acid molecules are deoxyoligonucleotides ("oligos"), highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may act at α1,2-fucosyltransferase gene regulation and/or as antisense primers in amplification reactions of α1,2-fucosyltransferase gene nucleic acid sequences. Further, such sequences may be used as part of ribozyme and/or triple helix sequences, also useful for α1,2-fucosyltransferase gene regulation. Still further, such molecules may be used as components of diagnostic methods whereby the presence of a pathogen or metastatic tumor cell may be detected.

The invention also encompasses (a) DNA vectors that contain any of the foregoing coding sequences and/or their complements (e.g., antisense); (b) DNA expression vectors that contain any of the foregoing coding sequences operatively associated with a regulatory element that directs the expression of the coding sequences; and (c) genetically engineered host cells that contain any of the foregoing coding sequences operatively associated with a regulatory element that directs the expression of the coding sequences in the host cell. As used herein, regulatory elements include, but are not limited to, inducible and non-inducible promoters, enhancers, operators and other elements known to those skilled in the art that drive and regulate expression.

The invention includes fragments of any of the DNA sequences disclosed herein. Fragments of the α1,2-fucosyltransferase gene corresponding to coding regions of particular domains, or in which one or more of the coding regions of the domains is deleted, are useful. Such α1,2-fucosyltransferase gene fragments may encode truncated gene products that retain a biological activity of the full-length α1,2-fucosyltransferase polypeptide, such as α1,2-fucosyltransferase activity or immunogenicity. The invention also includes mutant α1,2-fucosyltransferase genes encoding substitutions of amino acids as described below.

In addition to the gene sequences described above, homologs of such sequences, as may, for example, be present in other species, including humans, may be identified and may be readily isolated, without undue experimentation, by molecular biological techniques well known in the art. Further, there may exist genes at other genetic loci within the genome that encode proteins which have extensive homology to one or more domains of such gene products. These genes may also be identified via similar techniques.

The α1,2-fucosyltransferase gene and its homologs can be obtained from other organisms thought to contain α1,2-fucosyltransferase activity. For obtaining cDNA, tissues and cells in which α1,2-fucosyltransferase is expressed are optimal. Tissues which can provide a source of genetic material for α1,2-fucosyltransferase and its homologs, therefore, include intestinal mucosal cells and tumorigenic cells. For example, the isolated α1,2-fucosyltransferase gene sequences may be labeled and used to screen a cDNA library constructed from mRNA obtained from the organism of interest. The hybridization conditions used should be of a lower stringency when the cDNA library is derived from an organism different from the type of organism from which the labeled sequence was derived. Alternatively, the labeled fragment may be used to screen a genomic library derived from the organism of interest, again, using appropriately stringent condition. Low stringency conditions are well known in the art, and will vary predictably depending on the specific organism from which the library and the labeled sequences are derived. For guidance regarding such conditions see, for example, Sambrook et al., 1989, *Molecular Cloning, a Laboratory Manual,* Cold Springs Harbor Press, N.Y.; and Ausubel et al., 1989, *Current Protocols in Molecular Biology,* Green Publishing Associates and Wiley Interscience, N.Y.

Further, a previously unknown α1,2-fucosyltransferase gene type sequence may be isolated by performing PCR using two degenerate oligonucleotide primer pools designed on the basis of amino acid sequence within the gene of interest. The template for the reaction may be cDNA obtained by reverse transcription of mRNA prepared from human or non-human cell lines or tissue known or suspected to express a α1,2-fucosyltransferase gene.

The PCR product may be subcloned and sequenced to ensure that the amplified sequences represent the sequences of a α1,2-fucosyltransferase gene-like nucleic acids sequences. The PCR fragment may then be used to isolate a full length cDNA clone by a variety of methods. For example, the amplified fragment may be labeled and used to screen a bacteriophage cDNA library. Alternatively, the labeled fragment may be used to screen a genomic library.

PCR technology may also be utilized to isolate DNA sequences, including full length cDNA sequences. For example, RNA may be isolated, following standard procedures, from an appropriate cellular or tissue source. A reverse transcription reaction may be performed on the RNA using an oligonucleotide primer specific for the most 5' end of the amplified fragment for the priming of first strand synthesis. The resulting RNA/DNA hybrid may then be "tailed" with guanidines using a standard terminal transferase reaction, the hybrid may be digested with RNase H, and second strand synthesis may then be primed with a poly-C primer. Thus, cDNA sequences upstream of the amplified fragment may easily be isolated. For a review of cloning strategies which may be used, see e.g.,Sambrook et al., 1989, *Molecular Cloning, a Laboratory Manual,* Cold Springs Harbor Press, N.Y.

In cases where the α1,2-fucosyltransferase gene identified is the normal, or wild type, gene, this gene may be used to isolate mutant alleles of the gene. Mutant alleles may be isolated from individuals either known or proposed to have a genotype which contributes to intestinal mucosal disease and/or tumorigenicity. Mutant alleles and mutant allele products may then be utilized in the therapeutic and diagnostic systems described below.

A cDNA of the mutant gene may be isolated, for example by PCR. In this case, the first cDNA strand may be synthesized by hybridizing an oligo-dT oligonucleotide to mRNA isolated from tissue known or suspected to be expressed in an individual putatively carrying the mutant allele, and by extending the new strand with reverse transcriptase. The second strand of the cDNA is then synthesized using an oligonucleotide that hybridizes specifically the 5' end of the normal gene. Using these primers, the product is then amplified via PCR, cloned into a suitable vector, and subjected to DNA sequences analysis through methods known in the art. By comparing the DNA sequence of the mutant gene to that of the normal gene, the mutation(s) responsible for the loss or alteration of function of the mutant gene product can be ascertained.

A variety of host-expression vector systems may be utilized to express the α1,2-fucosyltransferase gene coding sequences of the invention. Such host-expression systems represent vehicles by which the coding sequences of interest may be produced and subsequently purified, but also represent cells which, when transformed or transfected with the appropriate nucleotide coding sequences, exhibit the α1,2-fucosyltransferase gene product of the invention in situ. These hosts include, but are not limited to, microorganisms such as bacteria (e.g., *E. coli, B. subtilis*) transformed with recombinant bacteriophage DNA, plasmid DNA or cosmid DNA expression vectors containing α1,2-fucosyltransferase gene product coding sequences; yeast (e.g. Saccharomyces, Pichia) transformed with recombinant yeast expression vectors containing the α1,2-fucosyltransferase gene product coding sequences; insect cell systems infected with recombinant virus expression vectors (e.g., baculovirus) containing the α1,2-fucosyltransferase gene product coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing α1,2-fucosyltransferase gene product coding sequences; or mammalian cell systems (e.g., COS, SHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the α1,2-fucosyltransferase gene product being expressed. For example, when a large quantity of such a protein is to be produced, for the generation of pharmaceutical compositions of α1,2-fucosyltransferase polypeptide or for raising antibodies to α1,2-fucosyltransferase polypeptide, for example, vectors which direct the expression of high levels of fusion protein products that are readily purified may be desirable. Such vectors include, but are not limited to the *E. coli* expression vector pUR278 (Ruther et al., 1983, *EMBO J.* 2:1791), in which the α1,2-fucosyltransferase gene product coding sequence may be ligated individually into the vector in frame with the lac z coding region that a fusion protein is produced; pIN vectors (Inouye & Inouye, 1985, *Nucleic Acids Res.* 13:3101–3109); and the like. pGEX vectors may also be used to express foreign polypeptide as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa colifornica* nuclear polyhedrosis virus (AcNPV) is used as a vector to express foreign genes. The virus grows in *Spodoptera frugiperday* cells. The α1,2-fucosyltransferase gene coding sequence may be cloned individually into non-essential regions (for example the polyhedrin gene) of the virus and placed under the control of an AcNPV promoter. Successful insertion of α1,2-fucosyltransferase gene coding sequence will result in inactivation of the polyhedrin gene and production of non-occluded recombinant virus. These recombinant viruses are then used to infect *S. frugiperda* cells in which the inserted gene is expressed.

In mammalian host cells, a number of viral-based expression systems may be utilized. In cases where an adenovirus is used as an expression vector, the α1,2-fucosyltransferase gene coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing α1,2-fucosyltransferase gene product in infected hosts (See Logan & Shenk, 1984, *Proc. Natl. Acad. Sci, USA* 81:3655–3659). Specific initiation signals may also be required for efficient translation of inserted α1,2-fucosyltransferase gene product coding sequences. These signals include the ATG initiation codon and adjacent sequences. In cases where an entire α1,2-fucosyltransferase gene, including its own initiation codon and adjacent sequences, is inserted into the appropriate expression vector, no additional translation control signals may be needed. However, in cases where only a portion of the α1,2-fucosyltransferase gene coding sequences is inserted, exogenous translational control signals, including, the ATG initiation codon must be provided.

Transfection via retroviral vectors, naked DNA methods and mechanical methods including micro injection and electroporation may be used to provide either stably transfected host cells (i.e., host cells that do not lose the exogenous DNA over time) or transient transfected host cells (i.e., host cells that lose the exogenous DNA during cell replication and growth).

An alternative fusion protein system allows for the ready purification of non-denatured fusion proteins expressed in human cell lines (Janknecht, et al., 1991, Proc. Natl. Acad. Sci. USA 88:8972–8976). In this system, the gene of interest is subcloned into a vaccinia recombination plasmid such that the gene's open reading frame is translationally fused to an amino-terminal tag consisting of six histidine residues. Extracts from cell infected with recombinant vaccinia virus are loaded onto $Ni^{2+}$ nitriloacetic acid-agarose columns and histidine-tagged proteins are selectively eluted with imidazole-containing buffers. The α1,2-fucosyltransferase gene products can also be expressed in transgenic animals. Animals of any species, including, but not limited to, mice, rats, rabbits, guinea pigs, pigs, micro-pigs, goats, and non-human primates may be used to generate α1,2-fucosyltransferase transgenic animals.

Expression Systems for α1,2-fucosyltransferase

The novel bacterial α1,2-fucosyltransferase encoded by the disclosed gene, and enzymatically active fragment thereof, can be used in the production of fucosylated oligosaccharides such as Lewis Y ($Le^y$) and Lewis B ($Le^B$). These bacterial oligosaccharides are structurally similar to certain tumor-associated carbohydrate antigens found in mammals. These product glycoconjugates also have research and diagnostic utility in the development of assays to detect mammalian tumors.

The fucosylated oligosaccharides may be produced by any number of methods utilizing the methods and compositions described herein. Standard enzymology techniques well known in the art may be utilized to develop systems to provide fucosylated oligosaccharides (see for example the *Methods in Enzymology*, volume series published by Academic Press; and Tim Bugg, "An Introduction to Enzyme and Coenzyme Chemistry" 1997, Blackwell Sciences, Inc.).

"Substrate" as used herein, means any material or combinations of different materials, that may be acted upon by the polypeptide of the invention to give rise to fucosylated oligosaccharides, for example, and not by way of limitation, substrates may include LacNAc-R and GDP-fucose.

Cells containing and cell-free systems may be used to produce the fucosylated oligosaccharides of the present invention. Cells containing and cell-free systems will be better understood in the description and examples that follow. Such systems are useful in the development of fucosylated oligosaccharides.

The present invention provides a method for synthesizing fucosylated oligosaccharides by reacting substrates in the presence of α1,2-fucosyltransferase, capable of catalyzing the formation of the fucosylated oligosaccharides from the substrates.

The α1,2-fucosyltransferase may be used regardless of its origin so long as it is capable of producing the fucosylated oligosaccharides from the substrates. The source of the α1,2-fucosyltransferase may be derived according to the methods and compositions as described herein, for example, through protein purification from host cells transfected with an expression system as described more fully below.

The substrates are allowed to react with the α1,2-fucosyltransferase polypeptide under suitable conditions to allow formation of the enzymatic product. Suitable conditions can be easily determined by one skilled in the art. For example, suitable conditions will include contacting the substrate and polypeptide for a sufficient time and under sufficient conditions to allow formation of the enzymatic product, e.g. $Le^y$, $Le^B$. These conditions will vary depending upon the amounts and purity of the substrate and enzyme, whether the system is a cell-free or cellular based system.

These variables will be easily adjusted by those skilled in the art. For example, the period of exposure of the enzyme to the substrate will be longer at lower temperatures, e.g., 4° C. rather than at higher temperatures. In the methods for synthesizing the fucosylated oligosaccharides there are no restriction in terms of the timing of the addition of the substrates. The ratios of the various substrates should be in equal proportions, i.e. 1:1. The ratios of the enzyme to the substrates may be varied depending upon the rate and quantity of fucosylated oligosaccharides desired.

The method of producing the fucosylated oligosaccharides may be carried out at temperatures of 4° C. to 60° C. Additionally, a number of buffers may be used, for example, and not by way of limitation, a buffer having a pH between 6.5 and 8.0, and in the presence of 15–30 mM $Mn^{2+}$. After a desired amount of fucosylated oligosaccharides are produced the α1,2-fucosyltransferase polypeptide may be inactivated by heating, centrifugal separation, or the like. The resulting fucosylated oligosaccharides may be further purified by techniques known to those skilled in the art.

Cell containing systems for the synthesis of fucosylated oligosaccharides may include recombinantly modified host cells according to the methods described below or may be naturally occurring cells which express α1,2-fucosyltransferase polypeptide or an enzymatically active portion thereof, so long as the cell is capable of catalyzing the synthesis of fucosylated oligosaccharides from substrates.

In the case of cell containing systems the host cell is contacted with the substrate, under conditions and for sufficient time to produce the oligosaccharide. The time and conditions will vary depending upon the host cell type and culture conditions and can be easily determined by those of skill in the art.

The invention provides a gene expression system for producing α1,2-fucosyltransferase polypeptides. The gene expression system comprises a host cell which has been modified with a polynucleotide encoding α1,2-fucosyltransferase polypeptide or a portion thereof, as described above.

A preferred gene expression system of the invention involves host cell modified with a polynucleotide encoding α1,2-fucosyltransferase polypeptide or a portion thereof.

The method involves culturing a gene expression system created according to the methods described above under conditions sufficient to produce the α1,2-fucosyltransferase polypeptide. The gene expression system comprises a host cell which has been recombinantly modified with a polynucleotide encoding a α1,2-fucosyltransferase polypeptide or a portion thereof.

The method is also directed to harvesting the α1,2-fucosyltransferase polypeptide. A further step of the method involves substantially purifying the harvested α1,2-fucosyltransferase. The purified α1,2-fucosyltransferase polypeptide may be used in the synthesis of fucosylated oligosaccharides or the preparation of antibodies as described above.

Specifically disclosed herein is a gene expression system recombinantly modified with a DNA sequence containing the α1,2-fucosyltransferase gene. The sequence contains an open reading frame (ORF) of approximately 900 base pairs which are transcribed into α1,2-fucosyltransferase product having a calculated molecular weight of 35,193 daltons.

As used herein, the term "recombinantly modified" means introducing a polynucleotide encoding α1,2-fucosyltransferase polypeptide into a living cell or gene expression system. Usually, the polynucleotide is present in a plasmid or other vector, although modification can also occur by uptake of free α1,2-fucosyltransferase polynucleotide or numerous other techniques known in the art.

As used herein, the term "gene expression system" means a living eukaryotic or prokaryotic cell into which a gene, whose product is to be expressed, has been introduced, as described above.

As used herein, the term "harvesting" means collecting or separating from the gene expression system the product produced by the inserted polynucleotide.

Polynucleotide sequences encoding α1,2-fucosyltransferase polypeptides can be expressed by polynucleotide transfer into a suitable host cell.

"Host cells" are cells in which a vector can be propagated and its DNA expressed. A gene expression system is comprised of a host cell in which a vector was propagated and the vector's DNA expressed. The term "host cell" also includes any progeny of the subject host cell. It is understood that all progeny may not be identical to the parental cell since there may be mutations that occur during replication. However, such progeny are included when the term "host cell" is used. Host cells which are useful in the claimed gene expression system and the claimed method of producing α1,2-fucosyltransferase polypeptide include bacterial cells, yeast cells fungal cells, plant cells and animal cells.

Methods of stable transfer, meaning that the foreign DNA is continuously maintained in the host, are known in the art. In the present invention, the α1,2-fucosyltransferase polynucleotide sequences may be inserted into a recombinant expression vector. The term "recombinant expression vector" refers to a plasmid, virus or other vehicle known in the art that has been manipulated by insertion or incorporation of the α1,2-fucosyltransferase genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Biologically functional viral and plasmid DNA vectors capable of expression and replication in a host are known in the art. Such vectors are used to incorporate DNA sequences of the invention.

The method of the invention produces α1,2-fucosyltransferase polypeptide which are substantially pure. As used herein, the term "substantially pure" refers to a protein which is free of other proteins, lipids, carbohydrates or other materials with which it is normally associated. One skilled in the art can purify α1,2-fucosyltransferase polypeptide using standard techniques for protein purification including preparative chromatography and immunological separations involving monoclonal or polyclonal antibodies. For example, the substantially pure α1,2-fucosyltransferase protein will yield a single major band of approximately 35 kD on a non-reducing polyacrylamide gel. The purity of the α1,2-fucosyltransferase polypeptide can also be determined by amino-terminal amino acid sequence analysis. α1,2-fucosyltransferase polypeptide include functional fragments of the polypeptide, so long as biological activity remains, such as α1,2-fucosyltransferase enzymatic activity. Accordingly, the invention includes a gene expression system and a method of producing α1,2-fucosyltransferase polypeptide which produce smaller peptides containing the enzymatic activity of α1,2-fucosyltransferase.

Production of α1,2-fucosyltransferase. Production of α1,2-fucosyltransferase from the gene expression system of the invention is achieved by culturing a gene expression system comprising a host cell recombinantly modified with a polynucleotide encoding α1,2-fucosyltransferase polypeptide or an enzymatically active portion thereof and harvesting the α1,2-fucosyltransferase polypeptide. The method further comprises substantially purifying the harvested α1,2-fucosyltransferase polypeptide using protein purification protocols well known in the art (*Current Protocols in Molecular Biology*, Chapter 10, eds. Ausubel, F. M. et al., 1994).

The method for producing α1,2-fucosyltransferase polypeptide involves culturing the gene expression system of the invention under conditions of continuous culture, such as, but not restricted to, "fed-batch cultures" or continuous perfusion cultures. Other continuous culture systems which find use in the present invention is set forth in Wang, G. et al. *Cytotechnology* 9:41–49, 1992; Kadouri, A. et al. *Advances in Animal Cell Biology and Technology for Bioprocesses*, pp. 327–330, Courier International, Ltd., 1989; Spier, R. E. et al. *Biotechnol. Bioeng.* 18:649–57, 1976.

Antibodies to α1,2-fucosyltransferase Proteins

Antibodies that define the α1,2-fucosyltransferase gene product are within the scope of this invention, and include antibodies capable of specifically recognizing one or more α1,2-fucosyltransferase gene product epitopes. Such antibodies may include, but are not limited to, polyclonal antibodies, monoclonal antibodies, humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above. Such antibodies may be used, for example, in the detection of α1,2-fucosyltransferase gene product in a biological sample, including, but not limited to, blood, plasma, and serum. Alternatively, the antibodies may be used as a method for the inhibition of abnormal α1,2-fucosyltransferase gene product activity. Thus, such antibodies may be utilized as part of treatment for intestinal mucosal disease, and may be used as part of diagnostic techniques whereby patients may be tested for abnormal levels of α1,2-fucosyltransferase gene products, or for the presence of abnormal forms of such proteins.

For the production of antibodies against a α1,2-fucosyltransferase gene product, various host animals may be immunized by injection with a α1,2-fucosyltransferase gene product, or a portion thereof. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsion, keyhole limpet hemocyanin, dinitrophenol, and potentially useful human adjuvants such as BCG, interferon and other cytokines effecting immunological response.

Polyclonal antibodies are a heterogenous population of antibody molecules derived from the sera of animals immunized with an antigen, such as a α1,2-fucosyltransferase gene product, or an antigenic functional derivative thereof. In general, for the production of polyclonal antibodies, host animals such as those described above, may be immunized by injection with α1,2-fucosyltransferase gene product supplemented with adjuvants as also described above.

Monoclonal antibodies (mAbs), which are homogenous population of antibodies to a particular antigen, may be obtained by any technique which provides for the production of antibody molecules by continuous cell lines in culture. These techniques include, but are not limited to, the hybridoma technique of Kohler and Milstein, (1975, Nature 256:495–497; and U.S. Pat. No. 4,376,110), human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclinal Antibodies and Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce single chain antibodies against α1,2-fucosyltransferase gene products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include but are not limited to: the F(ab')2 fragments which can be produced by pepsin digestion of the antibody molecule and the Fab fragments which can be generated by reducing the disulfide bridges of the F(ab')$_2$ fragments. Alternatively, Fab expression libraries may be constructed to allow rapid and easy identification of monoclinal Fab fragments with the desired specificity.

Methods of Detecting α1,2-fucosyltransferase in Biological Samples

The antibodies described above can be used in the detection of α1,2-fucosyltransferase polypeptides in biological samples. α1,2-fucosyltransferase polypeptide from blood or other tissue or cell type may be easily isolated using techniques which are well known to those of skill in the art. The protein isolation methods employed herein may, for example, be such as those described in Harlow and Lane (Harlow, E. and Lane, D., 1988, "Antibodies: A Laboratory Manual" Cold Spring Harbor Laboratory Press, Cold Spring Harbor, N.Y.), which is incorporated herein by reference in its entirety.

Preferred diagnostic method for the detection of wild type or mutant α1,2-fucosyltransferase polypeptides may involve, for example, immunoassays wherein α1,2-fucosyltransferase polypeptides are detected by their interaction with an anti-α1,2-fucosyltransferase polypeptide specific antibody.

For example, antibodies, or fragments of antibodies, such as those described above, useful in the present invention may be used to quantitatively or qualitatively detect the presence of wild type or mutant α1,2-fucosyltransferase polypeptides. This can be accomplished, for example, by immunofluorescence techniques employing a fluorescently labeled antibody coupled with light microscopic, flow cytometric, or fluorimetric detection. Such techniques are especially preferred if the α1,2-fucosyltransferase polypeptides are expressed on the cell surface.

The antibodies (or fragments thereof) useful in the present invention may, additionally, be employed histologically, as in immunofluorescence or immunoelectron microscopy, for in situ detection of α1,2-fucosyltransferase polypeptides. In situ detection may be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the α1,2-fucosyltransferase polypeptide, but also its distribution in the examined tissue. Using the present invention, those skill in the art will readily perceive that any of a wide variety of histological methods (such as staining procedures) can be modified in order to achieve such in situ detection.

Immunoassays for wild type or mutant α1,2-fucosyltransferase polypeptides typically comprise incubating a biological sample, such as a biological fluid, including but not limited to blood, plasma, or blood serum, a tissue extract, freshly harvested cells, or cells which have been incubate in tissue culture, in the presence of a detectably labeled antibody capable of identifying α1,2-fucosyltransferase polypeptides, and detecting the bound antibody by any of a number of techniques well known in the art.

Detection may also be accomplished using any of a variety of other immunoassays. For example, by radioactively labeling the antibody or antibody fragments, it is possible to detect wild type or mutant α1,2-fucosyltransferase polypeptides through the use of radioimmunoassays (RIA) (see, for example, Weintraub, Principles of Radioimmunoassays, Seventh Training Course on Radioligand Assay Techniques, The Endocrine Society, March, 1986, which is incorporated by reference herein). The radioactive isotope can be detected by such means as the use of a gamma counter or a scintillation counter or by autoradiography. It is also possible to label the antibody with a fluorescent compound such as fluorescein isothiocyanate, rhodamine, phycoerythrin, phycocyanin, allophycocyanin and fluorescamine.

The antibody can also be detectably labeled using fluorescence emitting metals such as $^{152}$Eu. Additionally the antibody may be detected by coupling it to a chemiluminescent compound such as luminol, isoluminol, theramatic acreidinium ester and oxalate ester.

The following examples are intended to illustrate but not limit the invention. While they are typical, other procedures known to those skilled in the art may alternatively be used to illustrate the embodiments and methods of the invention.

EXAMPLE 1

Cloning and sequence information of the *H. pylori* fucosyltransferase (fucT) gene Bacterial strains and Media.

*H. pylori* strains 26695 and UA802 were used for cloning, sequencing and mutagenesis of fucT2 genes. *H. pylori* cells were cultured on BHI-YE agar or in BHI-YE broth under microaerobic conditions (Ge and Taylor, 1997, *In Methods in Molecular Medicine*, C. L. Clayton and H. Mobley (eds). Totowa, N.J.: Humana Press, pp. 145–152). *E. coli* strain DH10B was used for production of recombinant plasmids. Cloning of *H. pylori* α(1,2) fucosyltransferase gene (Hp fucT2).

Figure 3A:
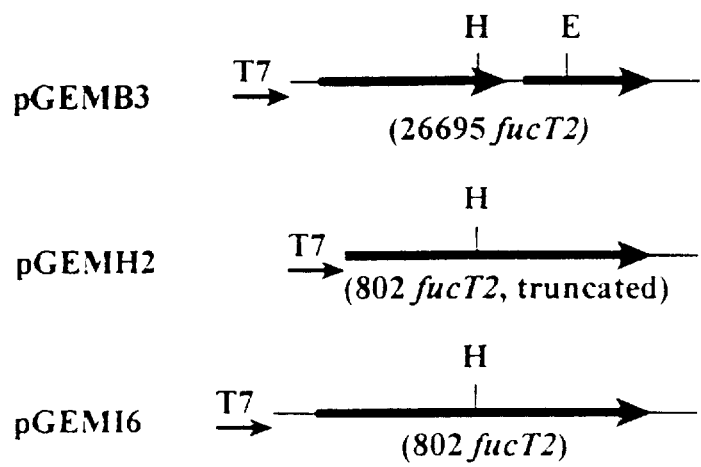
FIG. 3 shows the cloning and in vitro expression of Hp fucT2 genes. (A) Plasmid constructs containing intact or partial Hp fucT2 gene. Heavy arrows represent the predicted ORFs, and the thin lines indicate the flanking regions that had been cloned together with the coding region into the vector. The small arrows point to the direction of the transcription from the T7 promoter. Restriction endonuclease sites HindIII (H) and EcoRI (E) were used for constructing CAT insertion mutants. (B) Autoradiograph of a 0.1% SDS-12% PAGE analyzing the protein synthesis products from various plasmid constructs by E. coli T7 S30 extract. Lane 1, no DNA template. Some protein bands are from transcription-translation of endogenous DNA or RNA in the cell extract. Lane 2, pGEM-T vector. Lane 3, 4, and 5, plasmid constructs pGEMB3, pGEMH2, and pGEM16, respectively. The full length protein (33 KD) marked by the large arrow was overexpressed from intact fucT2 genes but not from 5'-truncated gene. A half-length protein (17 KD, marked by the small arrow) was also produced from 26695 fucT2, but not from 802 fucT2. Lane 6, 7, and 8, pGHC26, pGEC26, and pGHC8, plasmid mutants with CAT insertion at HindIII site of 26695 fucT2, at EcoRI site of 26695 fucT2, and at HindIII site of UA802 fucT2, respectively. All three plasmid mutants gave rise to strong expression of 24 KD CAT protein. The molecular mass markers (Life Technologies, Inc) are indicated on the right.

Two primers, GW44 (5'-GAACACTCACACGCGTCTT-3' (SEQ ID NO:3), position 99980–99962 in the published *H. pylori* genome) and GW32 (5'-TAGAATTAGACGCTCGCTAT-3'(SEQ ID NO:4), position 98855–98874 in the published *H. pylori* genome) were used to PCR amplify a 1.12 kb fragment containing Hp fucT2 from *H. pylori* 26695 and UA802 chromosomal DNA. In addition, by using a primer GW43 (5'-CGGAGGGCTTGGGAATCAA-3' (SEQ ID NO:5), position 99814–99796 in the published *H. pylori* genome) and primer GW32, a PCR fragment of 0.96 kb carrying 5'-truncated fuc T2 gene was obtained from UA802 chromosomal DNA. The PCR fragments were directly cloned into pGEM-T vector (Promega) following the manufacturer's instructions. The orientation of the genes cloned in the plasmids was examined by restriction enzyme analysis, and those clones with the fucT2 gene under the control of T7 promoter were selected. The resultant plasmids, pGEMB3, pGEMI6, and pGEMH2, are illustrated in FIG. 3A. Subsequently, the genes cloned in the plasmids were sequenced and were shown to be identical to the corresponding genes in the *H. pylori* genome.

Features of *H. pylori* α(1,2) fucT gene.

Based on the published *H. pylori* genome sequence (Tomb et al., 1997, Nature 388:539–547), a pair of primers, GW44 and GW32 (FIG. 1A) were designed. These primers were able to PCR amplify a DNA fragment (1.12 kb) from *H. pylori* strain UA802, which corresponds to the region containing HP0094 and HP0093 in 26695. The complete nucleotide sequence of this fragment is 95% identical to that of *H. pylori* 26695. However, it contains a single ORF encoding a protein of 300 amino acids with a calculated molecular weight of 35,193 daltons. We designated this gene Hp fucT2 to distinguish it from the previously identified α(1,3) fucT which was given a name of fucT (Martin et al., 1997,*J. Biol. Chem.* 272:21349–21356; Ge et al., 1997, *J. Biol. Chem.* 272:21357–21363). Hp fucT2 gene has a unique feature in its center region. In addition to a poly C tract identified previously (Tomb et al. 1997, *Nature* 388:539–547, Berg et al. 1997, *Trends Microbiol.* 12:468–474), we identified a sequence of TAA repeats (imperfect, may also be GAA or AAA) immediately following the poly C sequence (FIG. 1B). The changes of the repeat number of the both tracts contribute to the variation of the fucT2 genotype (on or off status) in different strains (FIGS. 1A, B and Table 2).

In an attempt to find out the relationship between the fucT2 gene and the Le$^Y$ phenotype, six additional *H. pylori* isolates were selected for analysis (Table 2). Together with the strains 26695 and UA802, these total eight strains fall into four groups of Lewis phenotypes: Le$^X$−/Le$^Y$+, Le$^X$+/Le$^Y$+, Le$^X$+/Le$^Y$−, and Le$^X$−/Le$^Y$−. The complete nucleotide sequences of the fucT2 genes from these strains demonstrated an extensive variation in the poly C and TAA repeat sequence among different strains, which make the gene either intact (as in UA802) or frameshifted (as in 26695). Like UA802 fucT2, UA1234 fucT2 encodes an intact ORF, even though there is a deletion of one TAA repeat. The existence of the intact fucT2 gene in UA802 and UA1234 is correlated to their Le$^Y$+ phenotype. UA1182, another example like 26695, contains a frameshift mutation in its fucT2 gene. This mutation could be compensated by translation frameshifting, since a dnaX-like translation frameshift cassette is present in frame.

The two strains with the Le$^X$+/Le$^Y$− phenotype, UA1174 and UA1218, displayed completely different features in their fucT2 genes. In UA1174 fucT2, there is the insertion of 2C and 2A at the hypermutable region, resulting in a frameshift mutation. Since a dnaX-like translation frameshift cassette is absent (the AAAAAG sequence is not in frame), the frameshift cannot be compensated, giving rise to a Le$^Y$– phenotype. On the other hand, UA1218 fucT2 encodes an intact ORF, because the changes in the hypermutable region do not create a frameshift. However, the result from the PCR and subsequent DNA sequencing revealed a deletion of 80 bp exactly in front of the SD sequence (ribosome binding site) of UA1218 fucT2 gene. Therefore, the Le$^Y$– phenotype of UA1218 could be attributed to the absence of the promoter for the expression of the fucT2 gene. The two strains in the last group, UA1207 and UA1210, have an intact fucT2 gene, since the deletion of one TAA repeat, or the change of (–C +A), respectively, does not create a frameshift. Therefore, the α(1,2) FucT in these two strains would be expected to be functional. From the Le$^X$– phenotype of these strains we can infer that their α(1,3) FucT may be not functional, which also leads to the Le$^Y$– phenotype.

Hp fucT2 gene has a unique feature in its center region which is responsible for the occurrence of the variant type of the gene in *H. pylori* 26695. It contains a poly C tract followed by imperfect TAA (or GAA, or AAA) repeats (FIG. 1B). UA802 fucT2 has a run of 12 Cs, which allows the initiating translation frame (0 frame) be read through this region, giving rise to a translation product of full length. In the case of 26695 fucT2, the existence of two more Cs (total 14 Cs) leads to early termination of the initiating frame (HP0094) at a TGA stop codon (FIG. 1B). Downstream of HP0094, there appears to be a potential start codon (ATG) in another frame which could be read to generate HP0093 (FIG. 1A).

Since the poly C tract was identified within the Hp fucT genes (both α1,3- and α1,2 fucT), it was believed that such simple oligonucleotide repeat regions are hypermutable and could offer an on-off mechanism for the expression of the gene (Saunders et al., 1998, *Mol. Microbiol.* 27:1091–1098), and may therefore be responsible for the phase variation of LPS expression. Indeed, the number of poly C repeats in Hp fucT2 gene is variable among different strains (N=11–14, the reference UA802 fucT2 has 12 Cs, Table 2). Additionally, we observed that the subsequent TAA repeat sequence (or called A-rich sequence) is also a mutation hotspot. The divergence at these repetitive sequences gave rise to the two types of the gene, encoding either a full-length product (hypothetically gene-on) or a truncated product(s) (hypothetically gene-off).

However, certain strains with a hypothetical off-status of the fucT2 gene have the Le$^Y$+ phenotype, as exemplified in 26695. The identification of a nucleotide sequence resembling the *E. coli* dnaX translation frameshift cassette within the 26695 fucT2 gene and the result of in vitro expression of the gene provide a reasonable mechanism by which the full-length protein could be produced by certain off-status fucT2 genes. Programmed translation frameshifts appear in genes from a variety of organisms and the frequency of frameshifting can be very high in some genes, approaching

TABLE 1

Characterization of *H. pylori* fucT2 mutants

| *H. pylori* strains[a] | ELISA reactivity (ODU)[b] with MAbs | |
|---|---|---|
| | anti-Le$^Y$ | anti-Le$^X$ |
| 26695 | 0.477 ± 0.047 (+) | 0.414 ± 0.042 (+) |
| 26695ΔH | 0.058 ± 0.014 (–) | 0.437 ± 0.016 (+) |
| 26695ΔE | 0.048 ± 0.025 (–) | 0.829 ± 0.038 (+) |
| UA802 | 0.63 ± 0.072 (+) | 0 ± 0.002 (–) |
| UA802ΔH | 0.03 ± 0.003 (–) | 0.144 ± 0.048 (+) |
| UA802ΔE | 0.069 ± 0.037 (–) | 0.336 ± 0.022 (+) |

[a]ΔH or ΔE represents *H. pylori* mutants carrying CAT insertion within the fucT2 gene at HindIII or EcoRI site.
[b]ELISA reactivity is expressed as the absorbance at 405 nm (ODU) and the values are averaged from triplicate determinations with standard deviation. Using the criteria of Wirth et al. (1996), the ODU over 0.1 units are considered positive, and the positivity/negativity is indicated in parentheses.

TABLE 2

Correlation of the fucT2 genotype with the LeY phenotype in various *H. pylori* strains.

| | Lewis phenotype[a] | | fucT2 genotype | | | proposed gene status[f] | | |
|---|---|---|---|---|---|---|---|---|
| strains | LeX | LeY | sequence divergence[b] | ORF[d] | translation frameshift[e] | fucT | fucT2 | ratio of FucT/FucT2 |
| UA802 | – | + | reference | intact | – | on/off | on | low |
| UA1234 | – | + | –(TAA) | intact | – | on/off | on | low |
| 26695 | + | + | +2C | frameshifted | + | on | off/on | high |
| UA1182 | + | + | –C | frameshifted | + | on | off/on | high |
| UA1174 | + | – | +2C, +2A | frameshifted | – | on | off | – |
| UA1218 | + | – | +C, –(AATA), and ΔP[c] | intact | – | on | off | – |
| UA1207 | – | – | –(TAA) | intact | – | off | on | – |
| UA1210 | – | – | –C, +A | intact | – | off | on | – |

[a]Lewis phenotype is based on the ELISA reading for each strain. For all the strains selected here, "–" represents the ELISA readings below 0.1 units, and "+" represents those over 0.3.
[b]Listed are the major changes of the sequence in the highly variable region (poly C and TAA repeats) in reference to UA802fucT2. Other base substitutions throughout the whole gene are easily identified to those skilled in the art. The sequences of the fucT2 genes from these strains have been deposited in the GenBank under the accession number AF076779 (UA802), AF093828 (UA1234), AF093829 (UA1182), AF093839 (UA1174), AF093831 (UA1218), AF093834 (UA1207), and AF0933833 (UA1210).
[c]ΔP indicates the deletion of a 80 bp-fragment in the promoter region of the gene.
[d]Due to the highly variable sequences, the ORF of fucT2 gene is either intact (complete) or frameshifted (truncated).
[e]Translation frameshift is predicted based on the sequences of the dnaX-like translation frameshift cassette identified in the individual fucT2 gene.
[f]FucT refers to the α(1,3)FucT. The model is described in detail in the Discussion.

100% (Farabaugh, 1996, *Annu. Rev. Genet.* 30:507–528). The best studied −1 frameshift model is *E. coli* dnaX, the gene for the τ_subunit of DNA polymerase III. As a result of translation frameshifting, a truncated product (γ_subunit of DNA polymerase III) is synthesized from dnaX in a frequency of about 40%–50% (Flower and McHenry, 1990, *Proc. Natl. Acad. Sci. USA* 87:3713–3717). Both τ and γ subunits are required for DNA synthesis, and are needed respectively for leading and lagging strand synthesis, due to their different processivity. The main element in dnaX translation frameshift cassette is A AAA AAG heptamer sequence in the appropriate reading frame. It has been shown that the efficient frameshifting at this sequence is due to the absence of tRNA$^{Lys}$ with a CUU anticodon in *E. coli* (Tsuchihashi and Brown, 1992, *Genes Dev.* 6:511–519). When the tRNA$^{Lys}$ with UUU anticodon encounters the AAG lysine codon it can easily slip to the −1 frame where it interacts with the AAA lysine codon more strongly. From the *H. pylori* whole genome sequence we know that *H. pylori* has only one tRNA$^{Lys}$ with a UUU anticodon. In addition, similar to those in the dnaX gene, the frameshift-stimulating elements including a putative SD sequence and a stem-loop structure were also found up- and downstream of the A AAA AAG sequence in 26695 fucT2 gene. Thus, it is very likely that certain *H. pylori* strains like 26695 use the same mechanism as *E. coli* dnaX gene to generate −1 frameshift in translation of their fucT2 genes. Although we have observed the full-length and half-length protein bands from the in vitro expression of 26695 fucT2 gene, the accurate frequency of translational frameshifting in this gene, as well as in the genes from different stains, has not yet been determined. Also, the expression of the gene in *H. pylori* cells could very well be different from that observed in vitro using *E. coli* T7 cell extract. Unlike α(1,3) fucosyltransferases, α(1, 2) FucTs belong to a more heterogenous family and display very weak homology. Multiple sequence alignment for eukaryotic and prokaryotic α(1, 2) FucTs allowed us to identify three highly conserved motifs that may have potential structural and/or catalytic importance. While motif I is located in the N-terminal stem region, motif II and III are located in the proposed catalytic domain (FIG. 2). By insertion mutagenesis we showed that the disruption of the gene at either the HindIII or EcoRI site abolishes its function in the synthesis of Le$^Y$, suggesting the integrity of the gene is necessary for this function.

Figure 5:
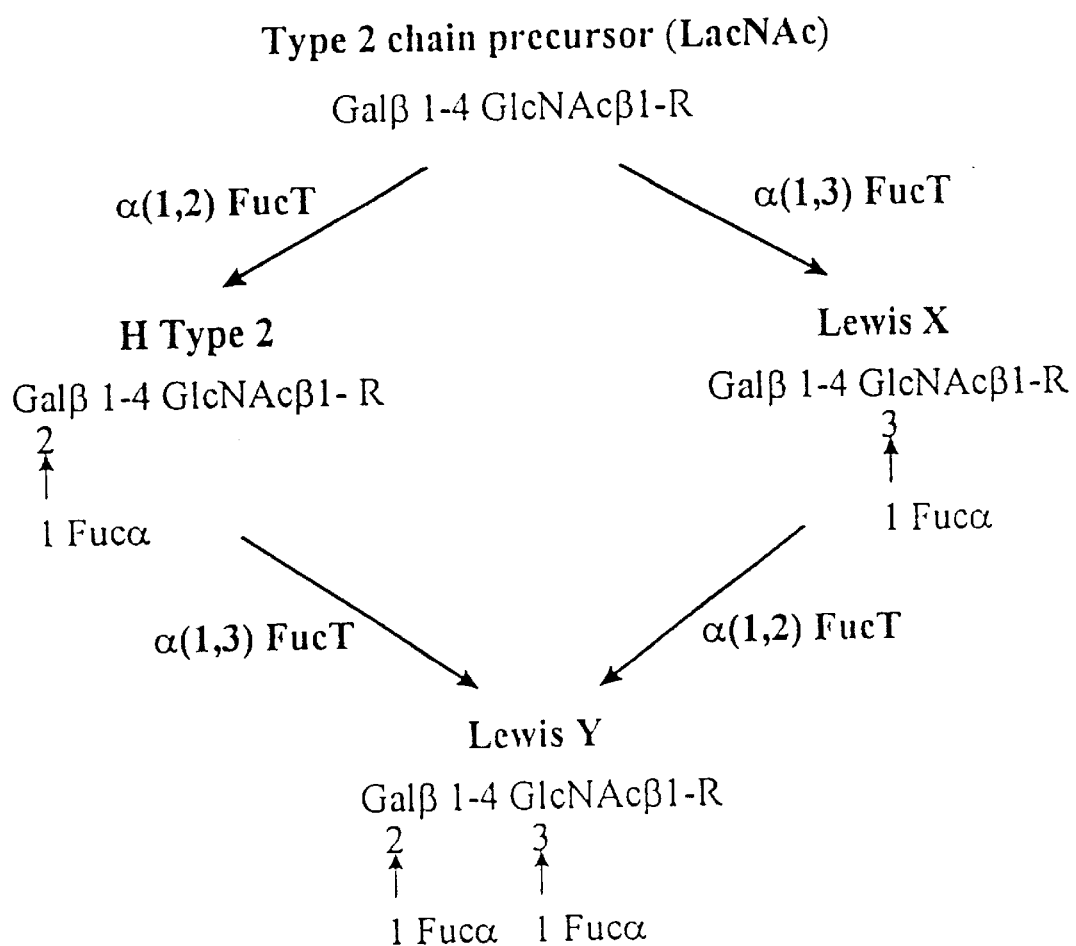
FIG. 5 shows two possible pathways for the synthesis of Lewis Y in *H. pylori*.

Unexpectedly, *H. pylori* fucT2 mutants express more Le$^X$ than the wild type cells. This finding suggests that Le$^X$ is the substrate for Le$^Y$ synthesis in *H. pylori*. In the commonly described mammalian system (Avent, 1997), Le$^Y$ is produced by addition of fucose through an α(1, 3) linkage on the H type 2 structure (FIG. 5, the pathway on the left). However, Martin et al. (1997) found that H type 2 is not the substrate for Hp α(1, 3) FucT, suggesting that in the synthesis of Le$^Y$ in *H. pylori*, α(1, 2) fucosylation may occur after α(1, 3) fucosylation (FIG. 5, the pathway on the right). Our results here are in good agreement with this notion. Thus, disruption of α(1, 2) FucT may result in the accumulation of its substrate, Le$^X$. Furthermore, there was a difference in the Le$^X$ expression between the two mutants carrying mutations at the HindIII or EcoRI site within fucT2 gene. The HindIII site is in the middle of fucT2 (type I) gene; downstream of it there exists a potential small ORF corresponding to HP0093 within which the EcoRI site is located. In this ORF, which may be expressed in the HindIII mutants, there possibly remains the active site or binding site, which may compete with α(1, 3) FucT for addition of fucose to make more Le$^X$. In contrast, the binding site of α(1, 2) FucT in the EcoRI mutants may be completely disrupted. Consequently, the increased Le$^X$ level is more evident.

Since the synthesis of Le$^Y$ requires both α(1, 3) FucT and α(1, 2) FucT activities (FIG. 5), turning off either gene will give rise to a Le$^Y$- phenotype, as seen in the strains UA1174, UA1218, UA1207, and UA1210 (Table 2). If both genes are on (or partially on), the levels of expression of Le$^X$ and Le$^Y$ will depend on the ratio of the concentrations (activities) of the two enzymes. Without knowing the actual status of α(1, 3) fucT gene (two copies), we assume that the ratio of α(1, 3)/α(1, 2) FucT in strains UA802 and UA1234 is low, so that the most (or all) of the Le$^X$ synthesized by α(1, 3) FucT was converted to Le$^Y$ by α(1, 2) FucT. This is supported by the observation that no Le$^X$ was detected from wild type UA802, while a low level of Le$^X$ was detected when the fucT2 gene was disrupted. In strains 26695 and UA1182, the fucT2 gene is in an off-on switching status due to the compensation by translational frameshifting. As seen from the in vitro expression of 26695 fucT2 gene and inferred from *E. coli* dnaX gene, the frequency of translation frameshift is presumably around 50%. Thus, the α(1, 2) FucT activity in 26695 could be lower than that in UA802. Since the fucT2 knock-out mutant of 26695 produced much more Le$^X$ than the corresponding UA802 mutant, we assume that the α(1, 3) FucT activity in 26695 is higher than that in UA802. Taken together, we propose that the ratio of α(1, 3)/α(1, 2) FucT activity in 26695 is high, which confers (Le$^X$+, Le$^Y$+) phenotype. To confirm this model, the genetic analysis for both copies of the α(1, 3) FucT gene and comparative determination of the activities of both enzymes from both strains are needed.

DNA sequencing and databases.

Both strands of appropriate PCR fragments or cloned DNA fragments were sequenced using the Thermo sequenase sequencing kit following the manufacturer's instructions (Amersham Life Science, Inc.). Sequence analyses were performed with the BLAST Program of the National Center of Biotechnology Information (Bethesda, Md.). The Wisconsin Package (version 9.0) of the Genetics Computer Group (GCG) (Madison, Wis.) was used for the editing of sequences.

Compared with the sequences in databases, Hp fucT2 has homologues in other bacteria: a gene (wbcH) within the LPS O-antigen gene cluster of *Yersinia enterocolitica* serotype O:8 (Zhang et al., 1997), and a gene (epsH) within the plasmid encoded eps gene cluster essential for exopolysaccharide biosynthesis in *Lactococcus lactis* (van Kranenburg et al., 1997, *Mol. Microbiol.* 24:387–397). Although both wbcH and epsH gene products could act as α(1,2) FucT enzymes as predicted from sequence homology, no experimental evidence for assignment of their function is yet available. Hp fucT2 gene product displays a low level of overall similarity in amino acid sequence to its eukaryotic as well as prokaryotic counterparts, with 18% identity to human Fut2 (Kelly et al., 1995, *J. Biol. Chem.* 270:4640–4649) and 22% identity to *Y. enterocolitica* WbcH. However, multiple sequence alignment revealed three blocks of highly conserved amino acid sequences within all the α(1,2) FucTs (motifs I, II, and III in FIG. 2), which may be important for the enzyme function. Among them, motif II is the one proposed to be a part of the nucleotide binding domain by Breton et al. (1998, *Glycobiology* 8:87–94). Note that this motif is missing from the deduced amino acid sequence of 26695 fucT2 gene, because the coding region is between HP0094 and HP0093.

Figures 2A, 2B:
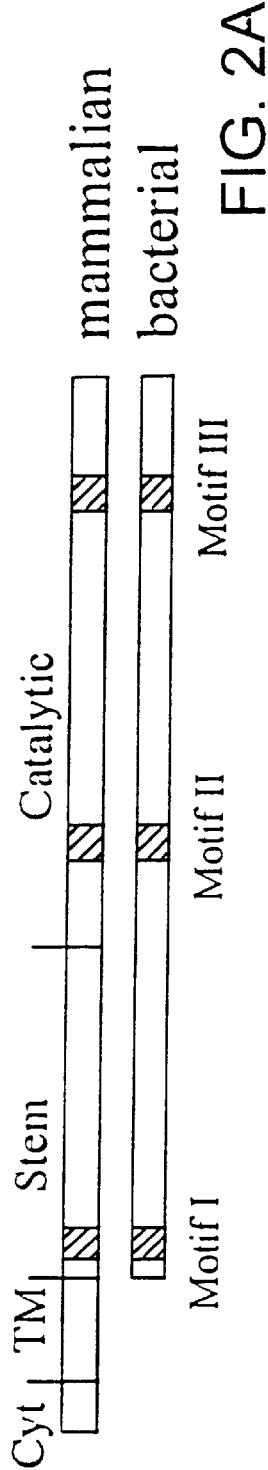
FIG. 2 shows an analysis of the deduced Amino acid (aa) sequence of Hp fucT2. (A) Schematic representation of the domain structures of mammalian and bacterial α(1,2) fucosyltransferases. Cyt, cytoplasmic. TM, transmembrane. Hatched boxes represent three highly conserved an sequence motifs. (B) Alignment of the three motifs of an sequences which are highly conserved in all prokaryotic and eukaryotic α(1,2) fucosyltransferases (Motif I sequences from top to bottom are SEQ ID NOs:9 to 13, respectively; Motif II sequences from top to bottom are SEQ ID NOs:14 to 18, respectively; and Motif III sequences from top to bottom are SEQ ID NOs: 19 to 23, respectively). The length (in aa) of each protein is given in parentheses after the name of organisms, and the positions of each motif within the protein are labeled in parentheses after each amino acid sequence. Ye, Y. enterocolitica. L1, Lactococcus lactis. Accession numbers of these sequences are: M35531 (man FUT1), U17894 (man FUT2), AF076779 (Hp FucT2, from the prototype fucT2 of UA802), U46859 (Ye WbsH), and U93364 (L1 EpsH).

All eukaryotic α(1,2) FucTs have a typical domain structure consisting of a short N-terminal cytoplasmic tail, a transmembrane domain, and a stem region followed by a large globular C-terminal catalytic domain (Kleene and Berger, 1993, Biochim Biophys Acta 1154:283–325). The three bacterial α(1,2) FucTs so far identified are shorter than the eukaryotic counterparts, and lack the N-terminal cytoplasmic tail and transmembrane domain (FIG. 2A). This is evident from the sequence alignment and by the analysis of the secondary structure of Hp FucT2 (hydropathy profile) which suggests it is a globular protein without any possible transmembrane domain. The N-terminal cytoplasmic tail and transmembrane domain of eukaryotic FucTs are proposed to have a role in Golgi localization and retention of the enzyme. The sequences of bacterial α(1,2) FucTs suggest that the enzyme is a soluble protein localized in the cytoplasm.

EXAMPLE 2

Plasmid constructs and Expression of the *H. pylori* fucT gene

Insertion mutagenesis and natural transformation.

Plasmid mutants carrying the disrupted *H. pylori* fucT2 gene were created by inserting the chloramphenicol acetyltransferase (CAT) cassette (Wang and Taylor, 1990, *Gene* 94:23–28) at HindIII or EcoRI site (FIG. 3A). Three mutant plasmids were obtained: pGHC26 (CAT cassette at HindIII site of 26695 fucT2), pGEC26 (CAT cassette at EcoRI site of 26695 fucT2), and pGHC8 (CAT cassette at HindIII site of UA802 fucT2). Plasmid mutants were introduced into the chromosome of *H. pylori* 26695 and UA802 by a natural transformation procedure. Four *H. pylori* fucT2 knock-out mutants were obtained: 26695ΔH, 26695ΔE, 802ΔH, and 802ΔE (Note: There is no EcoRI site in UA802 fucT2 gene, and 802ΔE was obtained by transforming pGEC26 into UA802.)

In vitro expression of Hp fucT2 gene.

The plasmids containing Hp fucT2 genes under the control of the T7 promoter, as well as those plasmids with CAT cassette insertion within the fucT2 genes, were purified by CsCl gradient ultracentrifugation. The purified supercoiled circular DNA were used as template for in vitro expression of the cloned genes using *E. coli* T7 S30 Extract System (Promega) following the manufacturer's instruction. The expressed gene products were labeled with [$^{35}$S] methionine and analyzed on 0.1% SDS-12% polyacrylamide gel followed by autoradiography.

Immunoelectron microscopy.

*H. pylori* broth cultures were absorbed onto Formvar-coated electron microscope grids and washed in phosphate buffer. The samples were incubated with primary anti-Le$^Y$ MAb isotype IgM (Signet Laboratories, Inc.) and further incubated with goat anti-mouse IgM-10 nm colloidal gold conjugate (EY Laboratories, Inc., San Mateo, Calif.). Positive labeling was determined by the presence of gold particles on unfixed and unstained *H. pylori* cells.

ELISA with *H. pylori* whole cell suspensions.

The primary antibodies used were anti-Le$^X$ (mAB BG-7) and anti-Le$^Y$ (mAB BG-8) (Signet Laboratories Inc. Dedham, Mass.). The secondary antibody was anti-mouse IgG+IgM conjugated to horse-radish peroxidase (HRP) (Biocan #115 035 068, Mississauga, Ontario) diluted 1:2000. The reaction was stopped with 4 mM sodium azide and the absorbance was recorded at 405 nm using a Titretek Multiscan MC (Helsinki, Finland) microtitre plate reader.

SDS-PAGE and immunoblot analysis of *H. pylori* LPS.

Proteinase K treated whole cells extracts of *H. pylori* strains were prepared and subjected to electrophoresis on a stacking gel of 5% acrylamide and a separating gel of 15% acrylamide. LPS on the gel was detected either by silver staining or by immunoblotting. The LPS transferred to nitrocellulose membrane (pore size 0.22 μm, Micron Separations Inc. Westboro Mass.) were probed with anti-Lewis structure antibodies (1:100 dilution), and subsequently with goat anti-mouse antibody conjugated to horse radish peroxidase (1:2000 dilution). Blots were developed using an enhanced chemiluminescence kit (Amersham) according to the manufacturer's specifications.

Both types of Hp fucT2 gene produce a full-length protein in vitro.

As illustrated in FIG. 3A and described in Experimental Procedures, Hp fucT2 genes were amplified by PCR and cloned into the pGEM-T vector under the control of a T7 promoter. The genes cloned into the plasmids are identical to those original genes in the *H. pylori* genome as verified by DNA sequencing. The plasmid pGEMB3 contains 26695 fucT2 gene; pGEMH2 contains a 5'-truncated 802 fucT2 gene; and pGEMI6 contains complete 802 fucT2 gene. Subsequently, the CAT cassette was inserted at the HindIII or EcoRI site within the cloned Hp fucT2 genes to obtain plasmid mutants pGHC26 (CAT cassette at HindIII site of 26695 fucT2), pGEC26 (CAT cassette at EcoRI site of 26695 fucT2), and pGHC8 (CAT cassette at HindIII site of UA802 fucT2). The six plasmid DNAs were used as templates for in vitro transcription-translation assays to examine the protein products encoded by the corresponding genes.

Figure 3B:
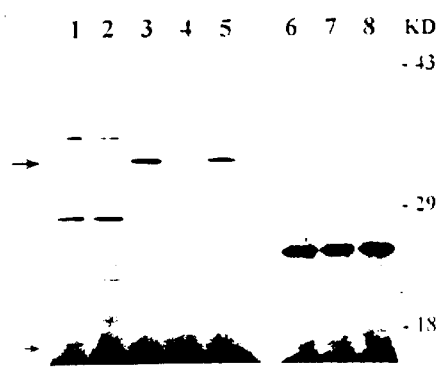

The expressed protein products analyzed on SDS-PAGE are shown in FIG. 3B. The expression of 802 fucT2 gene (pGEMI6, lane 5) gave rise to a major protein of 33 KD, which is very close to that expected from the deduced aa sequence (35 KD). Three weak bands with smaller molecular weights may result from translations starting at internal ATG codons or from degradation of the full length protein. As expected, 5'-truncated 802 fucT2 did not produce the full-length protein (pGEMH2, lane 4). For the expression of 26695 fucT2 (pGEMB3, lane 3), two small proteins of 18 and 13 KD were expected based on the DNA sequence of the gene. However, in addition to a 17 KD protein band which may represent the half-length gene product (HP0094), we observed a full-length (33 KD) protein band. To confirm that this result was not due to a mutation in the cloned gene, the sequence of the actual plasmid DNA (pGEMB3) used for the in vitro transcription-translation assay was re-examined, and no change was found compared to the original 26695 fucT2 gene.

The observation that 26695 fucT2 gene produces the full-length protein prompted us to consider other possibilities which could account for this result: RNA polymerase slippage in transcription or ribosome slippage in translation. By re-examining the DNA sequences of the simple repeat region within Hp fucT2 gene (FIG. 1B), we found three motifs (X XXY YYZ) typical of programmed translation frameshift (Farabaugh, 1996) occurred in the appropriate reading frame. The first one (C CCT TTA), located upstream of the poly C tract, exists in 26695 fucT2, but not in 802 fucT2. The second one (A AAA AAG), located downstream of the poly C tract, is present in the reading frame of 26695 fucT2, but not in the reading frame of 802 fucT2. This motif is identical to the extremely slippery heptanucleotide found in the MnRNA of *E. coli* dnaX (Flower and McHenry, 1990). Other elements of dnaX frameshifting signal (Larsen et al., 1994, *J. Bacteriol.* 176:6842–6851) including an upstream SD sequence and a downstream stem-loop structure which serve as stimulators of the frameshifting are also present in the deduced 26695 fucT2 mRNA sequence (FIG. 1C). Therefore, A similar mechanism for −1 frameshift as in dnaX is very likely at work in 26695 fucT2: exactly at the site behind the poly-C region where a frameshift has occurred (relative to the prototype 802 fucT2) and before encountering the stop codon, the reading frame could be shifted back (at a certain frequency) to the reading frame of the prototype gene, so that a full-length protein could be produced. Interestingly, just four codons before the HP0093 start codon, there exists another AAAA AAG sequence, both in 26695 and 802 fucT2 genes (FIG. 1B, line 4). However, no upstream SD sequence and downstream stem-loop structure were found around this slippery sequence.

Analysis of the fucT2 genes from several different strains (Table 2) demonstrated the various factors affecting expression of this gene and the ultimate Lewis phenotype. First, some divergence in the promoter region was observed among different strains, which could contribute to the differential expression of the gene through regulating transcription. Although the function of the promoter of Hp fucT2 gene was not performed in detail, apparently in strain UA1218 the promoter was completely missing resulting in the off-status of the gene. Second, two elements within the coding region of the gene were identified that could affect the coding ability of the gene. The first element, the simple sequence repeat region, is a mutation hotspot. As suggested previously (Tomb et al. 1997, Berg et al. 1997, Saunders et al. 1998), the frameshift mutation produced by DNA polymerase slippage during the replication of the gene may provide a mechanism for the switching between on and off status of the gene (at a frequency of <1%), which could account for the phase variation of $Le^Y$ expression reported by Appelmelk et al. (1998, *Infect. Immun.* 66:70–76). The extensive sequence divergence at this hypermutable region among various strains and the resulting two types (intact or frameshifted) of the gene support the notion that this strand-slippage mechanism occurs in *H. pylori*.

The second element within the gene is the slippery sequence for ribosome translation which is located immediately behind the hypermutable region. In certain strains that have a −1 frameshift mutation (relative to the prototype), such as 26695 and UA 1182, the translation could be shifted back to the prototype reading frame at a high frequency, producing functional proteins. In other strains that have a prototype reading frame (e.g. UA802) or +1 frameshift (e.g. UA1174), this slippery sequence is not in frame, thus is not functional. Therefore, the frameshift mutation in UA 1174 fucT2 cannot be compensated at the translation stage, resulting in the off-status of the gene. Interestingly, in the reading frame of the prototype fucT2 genes such as that of UA802 there exists another A AAA AAG slippery sequence in frame but without enhancing elements (FIG. 1B, line 4). It is not known whether translational frameshifting occur here at very low frequency to produce a minor fraction of truncated protein. If so, it could affect the level of the $Le^Y$ production, although insignificantly. In summary, it is propose that translational frameshifting may offer *H. pylori* an mechanism by which the full-length (active) and truncated (inactive or less efficient) enzymes can be produced in various ratios which account for the different levels of $Le^Y$ production among various strains. This ratio could also be influenced by certain environmental factors in the course of *H. pylori*-host interaction, leading to the varied level of $Le^Y$ expression in an individual strain.

Effect of fucT2 knock-out mutations on the expression of $Le^Y$ and $Le^X$ in *H. pylori*.

To demonstrate the requirement of Hp fucT2 in the biosynthesis of $Le^Y$, we performed insertion mutagenesis of fucT2. As described in Experimental Procedures, we constructed four *H. pylori* fucT2 knock-out mutants: 26695ΔH, 26695ΔE, 802ΔH, and 802ΔE, in which the fucT2 gene of *H. pylori* 26695 or UA802 was disrupted by insertion of a CAT cassette at HindIII or EcoRI site, respectively. The insertion of the CAT cassette at the specific location of the fucT2 gene in the *H. pylori* genome was verified by PCR amplification of an expected fragment and by DNA sequencing of the region surrounding the insertion site. The phenotypes of these *H. pylori* mutants for $Le^Y$ expression were examined by electron microscopy and by ELISA.

Figure 4:
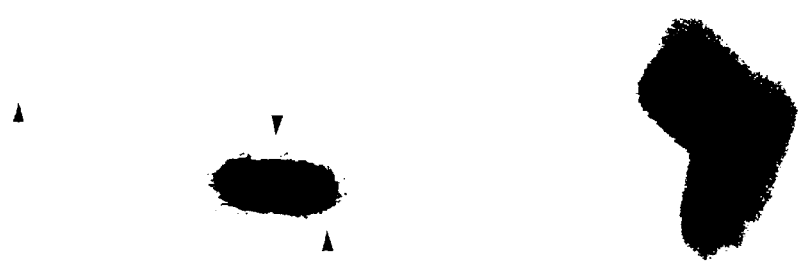
FIG. 4 shows a transmission electron micrographs of H. pylori UA802 and its isogenic mutant carrying CAT insertion within the fucT2 gene at HindIII (ΔH). Cells were incubated with anti-$Le^Y$ MAb and goat anti-mouse IgM-10 nm colloidal gold particles. Gold particles were present on the wild type cell (both on the cell wall and flagella sheath, marked by arrowheads) but absent on the mutant cell.
Figure 6A:
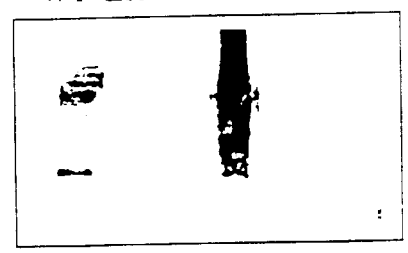
FIG. 6 shows an immunoblots of *H. pylori* LPS for detection of Lewis structures. Proteinase K treated whole cells extracts of *H. pylori* 26695 and UA802 wild type strains (WT) and their isogenic mutants (ΔH and ΔE) were resolved on SDS-PAGE and electroblotted onto a nitrocellulose membrane, and the LPS were immunostained using anti-Le$^Y$ (A) or anti-Le$^X$ antibody (B).
Figure 6B:
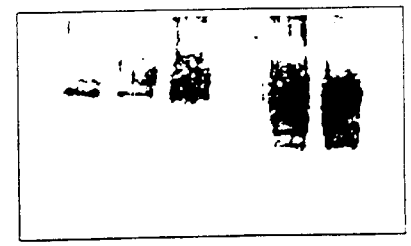

FIG. 4 shows an example of the transmission electron micrographs of UA802 wild type and mutant cells immunostained with anti-$Le^Y$ MAb. Wild type cells strongly express $Le^Y$, as evidenced by the presence of many gold particles. In contrast, the mutant cells, 802ΔH and 802ΔE (shown here is only 802_ΔH), were negative for immunogold labeling using anti-$Le^Y$ antibody. A similar pattern of electron micrographs for strain 26695 ($Le^Y$ positive) and its mutants ($Le^Y$ negative) was observed.

A quantitative examination for the expression of $Le^Y$ as well as $Le^X$ by these strains detected by ELISA is given in Table 1. Wild type strain 26695 expresses both $Le^Y$ and $Le^X$ (ODU=0.48 and 0.41, respectively), while wild type UA802 strongly expresses $Le^Y$ (ODU=0.63) but no $Le^X$. All of their isogenic mutants were negative for $Le^Y$ (ODU <0.1), suggesting that disruption of the fucT2 gene at both HindIII and EcoRI site abolish $Le^Y$ expression. Interestingly, there is an increase in the expression of $Le^X$ for the fucT2 mutants, especially when the mutation is at the EcoRI site.

Further characterization of these mutants was carried out by SDS-PAGE and immunoblots of the LPS for detection of $Le^Y$ and $Le^X$ (FIG. 5). Silver stained gels revealed no change in the LPS side chain length for all the mutants compared with the wild type cells. The immunoblots confirmed that $Le^Y$ is expressed by the wild type strains 26695 and UA802, and is no longer expressed in all the fucT2 mutant strains (FIG. 5A). Wild type UA802 does not express any $Le^X$ on its surface, but its isogenic fucT2 mutants do express $Le^X$ (FIG. 5B). There was no significant difference on the $Le^X$ expression levels between the two mutants (802ΔH and 802ΔE), which is different from the ELISA results. Since there is $Le^X$ expression in the wild type strain 26695, the increase of $Le^X$ expression in its mutant strains is not so evident. Similar to the ELISA results, however, a significant increase in $Le^X$ expression was observed in 26695ΔE, but not in 26695ΔH.

EXAMPLE 3
Enzymatic activities of *H. pylori* α1,2 fucosyltransferase
Overexpression of the *H. pylori* fucosyltransferase in E. coli.

In a typical experiment, *E. coli* CLM4 (pGP1–2) cells haboring a plasmid carrying an *H. pylori* fucT gene (pBKHp763fucT39, pGEMH2, pGEMI6 or pGEMB3) were grown in 25 ml liquid LB medium with appropriate antibiotics (kanamycin and ampicillin) at 30° C. to an optical density of 0.5–0.7 at 600 nm. After being collected, the cells were washed once with M9 medium, resuspended in 5 ml of supplemented M9 medium, and farther incubated at 30° C. for 1 h. To induce the expression of the fucT gene, the cell culture was shifted to 42° C. by adding 5 ml prewarmed (55° C.) supplemented M9 medium. After incubation at 42° C. for 15 min, rifampicin was added to a final concentration of 200 μg/ml, and cell growth was continued at 42° C. for 20 min.

For analysis of the protein on SDS-PAGE, a small aliquot (0.5 ml) of the cell culture was taken, and 2.5 μl of [$^{35}$S]-methionine (4.35×10$^{13}$ Bq/mmol, 3.7×10$^8$ Bq/ml, NEN™, Boston, Mass.) was added. After further growth at 30° C. for 30 min, the cells were harvested, resuspended in 100 μl sample buffer (50 mM Tris-HCl, pH6.8, 1% (w/v) SDS, 20 mM EDTA, 1% (v/v) mercaptoethanol, 10% (v/v) glycerol), and boiled for 3 min before loading on to the gel. For the preparation of the sample for the enzyme assay, the remaining part (major aliquot, 9.5 ml) of the cell culture after induction was further incubated at 30° C. for 30 min, then harvested. The cells were washed with 1.5 ml of 20 mM HEPES (pH 7.0), and resuspended in 1.5 ml of this buffer supplemented with 0.5 mM PMSF.

Preparation of cell lysates or cell extracts for the fucosyltransferase assay. The *E. coli* cells containing overproduced Hp FucT proteins, which were in HEPES buffer with PMSF as described above, were disrupted with a French press at 7000 lb/in² at 4° C. The cell lysates were used directly for enzyme assays. For determining the location of the enzyme activities, the cytoplasmic and membrane fractions were separated as follows. The cell lysates were centrifuged at 13,000× g at 4° C. for 10 min. The cell debris were discarded and the supernatant was subjected to ultracentrifugation at 128,000× g (Beckman TL100/rotor 100.2) at 4° C. for 1 h. The supernatant was collected as the cytoplasmic fraction. The membrane pellets were resuspended in a small volume of the same buffer and treated with 1 M NaCl.

Fucosyltransferase assay.

Assays of Hp α1,2 and α1,3 FucT activities were carried out according to the method described by Chan et al. (1995, Glycobiology 5:683–688) with some modifications. Reactions were conducted at 37° C. for 20 min in a volume of 20 μl containing 1.8 mM acceptor, 50 μM GDP-fucose, 60000 dpm GDP-[$^3$H]fucose, 20 mM HEPES buffer (pH7.0), 20 mM MnCl$_2$, 0.1 M NaCl, 35 mM MgCl$_2$, 1 mM ATP, 5 mg/ml BSA, and 6.2 μl of the enzyme preparation. The acceptors used in this study were: LacNAc [βGal 1–4 βGlcNAc], Le$^X$ [βGal 1–4 (α Fuc1–3) βGlcNAc], Type 1 [μGal 1–3 βGlcNAc], and Le$^a$ [βGal 1–3 (α Fuc1–4) βGlcNAc]. GDP-[$^3$H]fucose (1.9×10$^{11}$ Bq/ml/mmol) was obtained from American Radiolabeled Chemicals Inc. (St. Louis, Mo.). Sep-Pak Plus C-18 reverse-phase cartridges were purchased from Waters (Mississauga, ON). For calculation of the specific activity of the enzyme (micro-units per milligram protein), protein concentrations of the cell extracts were determined with a BCA protein assay kit (Pierce, Rockford, Ill.) using BSA as a standard according to the supplier's instructions.

Acceptor specificity of Hp α1,2 FucT.

Plasmid pGEMI6 carries the prototype fucT2 gene from *H. pylori* UA802 which produces a high level of Le$^Y$. Initially, we quantitated the α1,2 FucT activity by using LacNAc and Le$^X$ as acceptors, the two potential substrates of α1,2 FucT for the synthesis of Le$^Y$ (FIG. 5). Surprisingly, almost no activity was detected using LacNAc as an acceptor, whereas considerable activity was observed for the monofucosylated Le$^X$ acceptor (Table 3B). The specific activity of α1,2 FucT is much lower compared to that of α1,3 FucT (Table 3A).

In mammalian cells, the same α1,2 FucT enzyme (H or Se, tissue-specific) is normally responsible for the synthesis of both H type 1 and H type 2 structures (Sarnesto et al., 1990, *J. Biol. Chem.* 265:15067–15075; Sarnesto et al., 1992, *J. Biol. Chem.* 267:2732–2744). To determine whether the Hpα1,2 FucT is also involved in the synthesis of Le$^b$, we measured its activity with type 1 oligosaccharide acceptors (Table 3B). Even though UA802 does not express type 1 Lewis antigen, its α(1,2) FucT enzyme can transfer fucose to Type 1 and Le$^a$ acceptors. Compared to Le$^X$, type 1 and Le$^a$ are even more efficient substrates for Hp α1,2 FucT (2-fold more active). Thus, Hp α1,2 FucT can also synthesize H type 1 and Le$^b$.

TABLE 3

Activity and acceptor specificity of *H. pylori* fucosyltransferases

| | Overexpressed protein[a] (plasmid construct) | acceptor | proposed product | specific activity (μU/mg)[b] | relative activity (%)[c] |
|---|---|---|---|---|---|
| A | α1,3 FucT (pBKHp763fucT39) | LacNAc | Le$^X$ | 1480 | |
| B | α1,2FucT (UA802) (pGEMI6) | LacNAc | H type 2 | 14 ± 8 | 4.5 |
| | | Le$^X$ | Le$^Y$ | 150 ± 33 | 49 |
| | | Type 1 | H type 1 | 309 ± 28 | 100 |
| | | Le$^a$ | Le$^b$ | 301 ± 13 | 97 |

[a]*E. coli* whole cell extract containing the overexpressed *H. pylori* FucT protein was used for the enzyme assay.
[b]A micro-unit (mU) of the enzyme is expressed as the amount of enzyme that converts 1 pmol of acceptor to product per min. Specific activity was obtained by dividing the total activity (mU) by the total protein content (mg) in the whole cell extract. The data were averaged from at least three independent determinations with standard deviation as shown.
[c]% activity relative to that of UA802 α1,2 FucT on its best substrate Type 1.

Analysis of the reaction products of Hp α1,2 FucT by capillary electrophoresis.

Figure 7A:
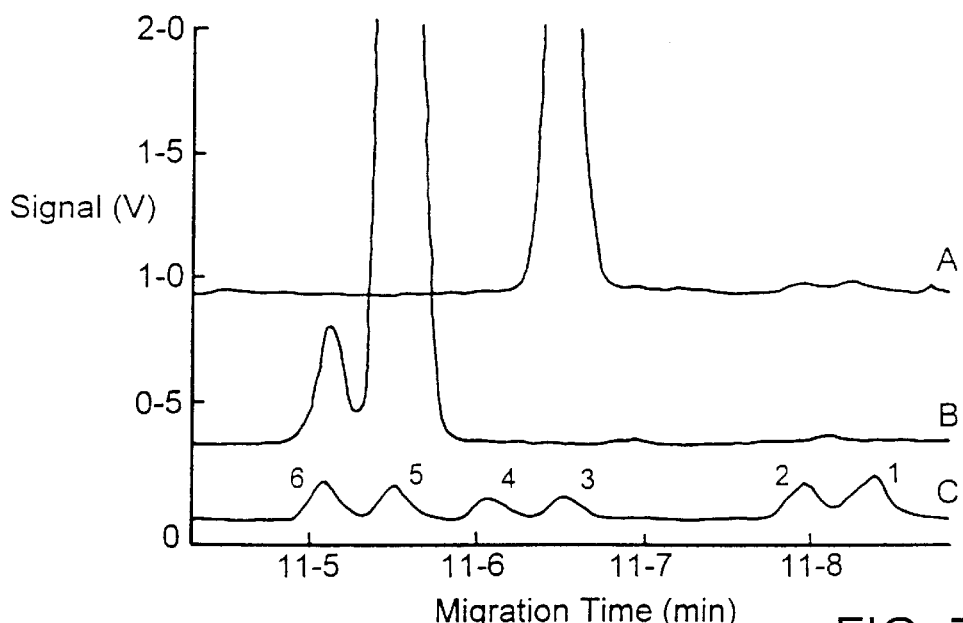
FIG. 7 shows identification of the reaction products of Hp α1,2-fucosyltransferase by capillary electrophoresis. The enzyme used here was the overexpressed UA802 α1,2-fucosyltransferase polypeptide. The reactions were carried out as described in Example 3 below. (A) The reaction of type 2 substrates LacNac (line a) and Le$^X$ (line b). (B) The reactions on Type 1 substrates (line d) and Le$^B$ (line e). Line c and f represent the standard TMR-labeled oligosaccharides: (1) linking arm, (2) GlcNAc, (3) LacNAc, (4) H type 2, (5) Le$^X$, (6) Le$^Y$, (7) Type 1, (8) H type 1, (9) Le$^A$, and (10) Le$^B$. All electropherograms are Y-offset for clarity.
Figure 7B:
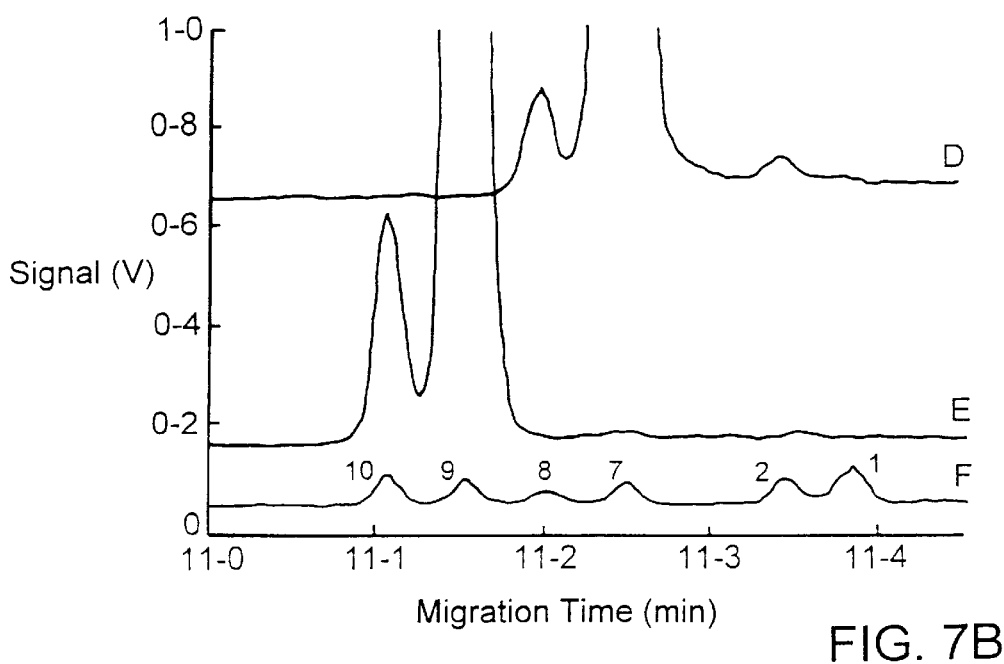

The reaction products synthesized from different acceptors by the Hp α1,2 FucT were further characterized by capillary electrophoresis with laser-induced fluorescence detection. The reaction mixture contained the overproduced UA802 α1,2 FucT protein (from pGEMI6 clone), GDP-fucose, and different acceptors labeled with tetramethylrhodamine (TMR). The results (FIG. 7) confirmed the data from the enzyme assay using radioactive labeled GDP-fucose (Table 3B) by identifying the products of the reactions.

When using LacNAc as an acceptor (FIG. 7A, line a), no reaction product representing H type 2 was observed, suggesting that LacNAc is not a substrate for Hp α1,2 FucT. In the reaction using Le$^X$ as an acceptor (FIG. 7A, line b), a small new peak was produced, which co-migrated with a synthetic Le$^Y$-TMR (standard Le$^Y$) in the electropherogram, indicating that this new peak represents the Le$^Y$ product synthesized from Le$^X$ by Hp α1,2 FucT. Similarly, by using Type 1 or Le$^a$ as acceptors (FIG. 7B), new peaks co-migrating with authentic products, H type 1 or Le$^b$ respectively, were observed. As negative controls, the protein extract from the *E. coli* CLM4 (pGP 1–2) clone containing the pGEM vector without Hp fucT2 gene was used in the reactions for each acceptor tested above, and no peaks for the products of α1,2 FucT were observed.

Novel α1,2 fucosyltransferase.

Figure 8A:
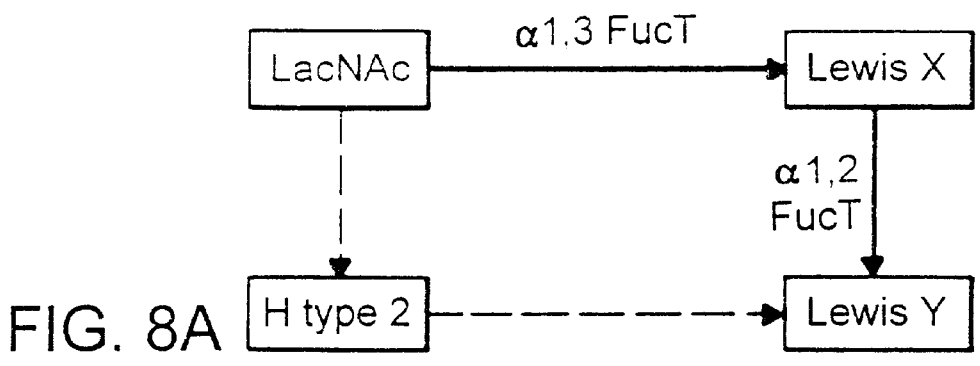
FIG. 8 shows identified pathways for the synthesis of Lewis antigens in *H. pylori*. Lewis structures known to be expressed on the *H. pylori* cell surface are boxed. Solid arrows represent the fucosyltransferase activities that have been demonstrated in this study, and the thickness of the arrows indicates the relative level of the enzyme activity. (A) *H. pylori* strains predominantly express Le$^X$ and Le$^Y$, and do not appear to express H type 2. It seems reasonable that *H. pylori* utilizes Le$^X$ to synthesize Le$^Y$. For operation of this pathway *H. pylori* normally maintains a higher level of α1,3-fucosyltransferase than of α1,2-fucosyltransferase. (B) *H. pylori* α1,2-fucosyltransferase has the ability to transfer fucose to Type 1 as well as to Le$^A$. The synthesis of Le$^B$ requires the concerted action of α1,2-fucosyltransferase with an α1,4-fucosyltransferase.

Determination of activities of the responsible fucosyltransferases is direct proof to distinguishing between the two possible pathways (FIG. 5). The observation in this study that Le$^X$ but not LacNAc is the substrate for the Hp α1,2 FucT clearly indicated that *H. pylori* prefers to use the Le$^X$ pathway to synthesize Le$^Y$ (FIG. 8A). Other supporting evidence came from the enzyme assay for Hp α1,3 FucT: (I) LacNAc is an excellent substrate for Hp α1,3 FucT (Ge et al., 1997; Martin et al., 1997; and Table 3A); and (ii) Martin et al. (1997) found that H type 2 was not the substrate of an Hp α1,3 FucT. It should be noted, however, that the fucosyltransferases from different *H. pylori* strains may have different acceptor specificity. Further studies on combined analysis of the α1,3 and α1,2 FucTs from various *H. pylori* strains are needed to elucidate whether this novel pathway for the synthesis of Le$^Y$ is general in *H. pylori* or is strain-specific.

Figure 8B:
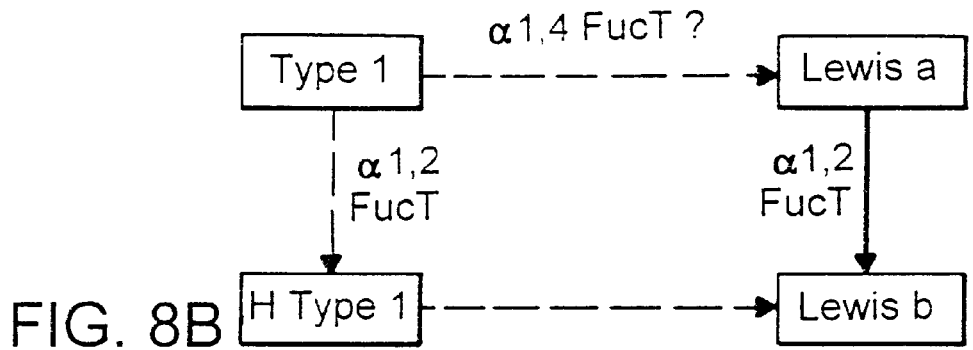

In addition to its function in Le$^Y$ synthesis, Hp α1,2 FucT is also active on type 1 Lewis structures (summarized in FIG. 8B). This provides a basis for the recent finding that Type 1 (Le$^c$), H type 1, and Le$^a$ are expressed in certain *H.* pylori strains (Le$^b$ was also detected in some strains by serological methods but has not yet been confirmed by structural analysis) (Monteiro et al., 1998, *J. Biol. Chem.* 273:11533–11543). Here again, the activity of the Hp α1,2 FucT to synthesize Le$^b$ from Le$^a$ indicated that this bacterial enzyme is different from the normal mammalian counterparts which cannot use Le$^a$ as substrate. To know if Le$^b$ can be synthesized from H type 1 in *H. pylori* awaits the detection of an α1,4 FucT. The α1,2 FucT characterized in this study is from *H. pylori* strain UA802 which does not produce any type 1 Lewis antigen. This suggests that the same α1,2 FucT enzyme could be used in the strains that produce type 1 epitopes. The failure to produce type 1 Lewis antigens in many *H. pylori* strains could be due to the inavailability of one of the other enzymes involved in the synthesis of Lewis antigens such as galactosyltransferase that adds βGal to GlcNAc or α1,3/4 FucT that places the αFuc unit at βGlcNAc.

In summary, in contrast to the normal mammalian α1,2 FucT (H or Se enzyme), Hp α1,2 FucT prefers to use Lewis X [βGal 1–4 (αFuc1–3) βGlcNAc] rather than LacNAc [βGal 1–4 βGlcNAc] as a substrate, suggesting that *H. pylori* uses a novel pathway (via Lewis X) to synthesize Lewis Y. Hp α1,2 FucT also acts on type 1 acceptor [βGal 1–3 βGlcNAc] and Lewis a [βGal 1–3 (αFuc1–4) βGlcNAc], which provides *H. pylori* with the potential to synthesize H type 1 and Lewis b epitopes. The ability to transfer fucose to a monofucosylated substrate (Lewis X or Lewis a) makes Hp α1,2 FucT distinct from normal mammalian α1,2 FucT.

Hp α1,2 FucT is a soluble protein.

DNA sequence analysis predicted the Hp α1,2 FucT to be a hydrophilic protein, and the same is true for Hp a 1,3 FucT (Ge et al., 1997). However, the determination of Hp α1,3 FucT activity from the overexpressed proteins demonstrated that the majority of the activity were present in the membrane fraction (Ge et al., 1997). To delineate the cellular location of the Hp α1,2 FucT activity, cytoplasmic and membrane fractions of *E. coli* cells overproducing Hp α1,2 FucT proteins were prepared as described in Materials and Methods. The activity in both fractions was determined using Le$^X$ or Type 1 as acceptors (Table 4). There was no detectable activity in the membrane fraction when using Le$^X$ as an acceptor. By using Type 1 as an acceptor, a very low amount of activity (negligible) was detected in the membrane fraction, which accounts for less than 3% of the total activity. These results indicated that Hp α1,2 FucT is a soluble cytoplasmic protein.

TABLE 4

Enzyme activities of *H. pylori* α1,2 FucT in cytoplasmic and membrane fractions.

| Exp. No. | Acceptor used | protein fraction[a] | specific activity (μU/mg protein) | total activity (μU)[b] | relative activity (%)[c] |
|---|---|---|---|---|---|
| 1 | Le$^x$ | cytoplasm | 38 | 49 | 100 |
|   |        | membrane  | 0  | 0  | 0   |
| 2 | Le$^x$ | cytoplasm | 41 | 54 | 100 |
|   |        | membrane  | 0  | 0  | 0   |
|   | Type 1 | cytoplasm | 78 | 108 | 100 |
|   |        | membrane  | 8  | 3  | 3   |

[a] As a typical experiment, each protein sample was prepared from 25 ml cell culture of *E. coli* CLM4 (pGP1-2, pGEMI6) containing the overexpressed UA802 α1,2 FucT. The cytoplasmic and membrane fractions were separated as described.
[b] Total activity (micro-units) in each protein sample derived from 25 ml cell culture.
[c] Percentage of the total activity in the cytoplasmic or membrane fraction.

What is claimed is:

1. An isolated polynucleotide comprising a fragment of SEQ ID NO: 1 that encodes a α1,2-fucosyltransferase polypeptide that catalyzes the synthesis of Lewis Y and Lewis B.

2. The isolated polynucleotide of claim 1, wherein the polynucleotide comprises nucleotide bases 137–1036 of SEQ ID NO: 1.

3. The isolated polynucleotide of claim 1, wherein the α1,2-fucosyltransferase polypeptide comprises SEQ ID NO: 2.

4. An isolated polynucleotide that encodes a α1,2-fucosyltransferase polypeptide comprising SEQ ID NO: 2 or a bioactive fragment thereof, wherein the polypeptide or bioactive fragment has α1,2-fucosyltransferase activity and catalyzes the synthesis of Lewis Y and Lewis B.

5. The polynucleotide of claim 4, wherein the polynucleotide comprises a sequence having at least one repeat of the sequence X XXY YYZ, wherein X=A or C, Y=A or T and Z=A or G.

6. An isolated polynucleotide selected from the group consisting of:

(a) a polynucleotide comprising SEQ ID NO: 1;

(b) a polynucleotide comprising nucleotide 137–1036 of SEQ ID NO: 1, wherein "T" in the sequence is replaced with "U";

(c) a polynucleotide that hybridizes to a nucleic acid molecule comprising a sequence as set forth in SEQ ID NO: 1 under stringent conditions wherein said stringent conditions comprise hybridization at 68° C. in 0.5 M NaHPO$_4$, 7% sodium dodecyl sulfate (SDS), 1 mM EDTA at 65° C., and washing in 0.1×SSC/0.1% SDS, wherein the polynucleotide encodes a polypeptide having α1,2-fucosyltranferase activity and catalyzes the synthesis of Lewis Y and Lewis B;

(d) a polynucleotide comprising a nucleic acid sequences complementary to (i) SEQ ID NO: 1, (ii) SEQ ID NO: 1, wherein "T" in SEQ ID NO: 1 is replaced with "U", (iii) nucleotides 137–1036 of SEQ ID NO:1, or (iv) nucleotides 137–1036 of SEQ ID NO: 1, wherein "T" in the sequence is replace with "U".

7. An isolated polynucleotide that hybridizes to a nucleic acid molecule comprising a sequence as set forth in SEQ ID NO: 1 under stringent conditions wherein said stringent conditions comprise hybridization at 68° C. in 0.5 M NaHPO$_4$, 7% sodium dodecyl sulfate (SDS), 1 mM EDTA at 65° C., and washing in 0.1×SSC/0.1% SDS, wherein the polynucleotide encodes a polypeptide having α1,2-fucosyltranferase activity and catalyzes the synthesis of Lewis Y and Lewis B.

8. A vector comprising a polynucleotide as set forth in claim 6.

9. The vector of claim 8, wherein the vector is an expression vector.

10. An isolated nucleic acid molecule encoding a fusion polypeptide, the nucleic acid molecule comprising a polynucleotide as set forth in claim 6 operably linked to a polynucleotide encoding polypeptide or peptide of interest.

11. A host cell transformed or transfected with a polynucleotide of claim 6.

12. A host cell transformed or transfected with the vector of claim 8.

13. A method for producing an α1,2-fucosyltransferase polypeptide, comprising:

culturing the host cell of claim 11 under conditions such that a recombinant α1,2-fucosyltransferase polypeptide is expressed from the polynucleotide; and isolating the α1,2-fucosyltransferase polypeptide.

14. A method for producing an α1,2-fucosyltransferase polypeptide, comprising:

culturing the host cell of claim 12 under conditions such that a recombinant α1,2-fucosyltransferase polypeptide is expressed from the vector; and isolating the α1,2-fucosyltransferase polypeptide.

15. A method of producing a α1,2-fucosyltransferase fusion protein comprising:

culturing a host cell transfected or transformed with the nucleic acid molecule of claim 10 under conditions such that a recombinant α1,2-fucosyltransferase fusion polypeptide is expressed from the nucleic acid molecule; and isolating the α1,2-fucosyltransferase fusion protein.

* * * * *